US010130614B2

(12) United States Patent
Finegold

(10) Patent No.: US 10,130,614 B2
(45) Date of Patent: *Nov. 20, 2018

(54) METHOD FOR DIAGNOSING, PREVENTING, AND TREATING NEUROLOGICAL DISEASES

(71) Applicant: Department of Veterans Affairs, Washington, DC (US)

(72) Inventor: Sydney M. Finegold, Los Angeles, CA (US)

(73) Assignee: The United States of America as represented by the Department of Veterans Affairs, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/636,472

(22) Filed: Jun. 28, 2017

(65) Prior Publication Data

US 2017/0296518 A1 Oct. 19, 2017

Related U.S. Application Data

(62) Division of application No. 13/117,073, filed on May 26, 2011, now Pat. No. 9,707,207.

(60) Provisional application No. 61/275,714, filed on May 26, 2010.

(51) Int. Cl.
| | |
|---|---|
| *A61K 31/427* | (2006.01) |
| *A61K 31/397* | (2006.01) |
| *A61K 31/424* | (2006.01) |
| *A61K 31/431* | (2006.01) |
| *C12Q 1/18* | (2006.01) |
| *A61K 45/06* | (2006.01) |
| *A61K 31/43* | (2006.01) |
| *A61K 35/741* | (2015.01) |
| *A61K 35/745* | (2015.01) |
| *A61K 35/747* | (2015.01) |

(52) U.S. Cl.
CPC .......... *A61K 31/427* (2013.01); *A61K 31/397* (2013.01); *A61K 31/424* (2013.01); *A61K 31/43* (2013.01); *A61K 31/431* (2013.01); *A61K 35/741* (2013.01); *A61K 35/745* (2013.01); *A61K 35/747* (2013.01); *A61K 45/06* (2013.01); *C12Q 1/18* (2013.01); *Y02A 50/473* (2018.01)

(58) Field of Classification Search
CPC .......................... A61K 31/427; A61K 31/397
See application file for complete search history.

(56) References Cited

U.S. PATENT DOCUMENTS

| | | | |
|---|---|---|---|
| 4,710,379 A | 12/1987 | Kawai et al. | |
| 5,443,826 A | 8/1995 | Borody et al. | |
| 5,925,550 A | 7/1999 | Lancin et al. | |
| 5,948,402 A | 9/1999 | Keith et al. | |
| 6,203,797 B1 | 3/2001 | Perry | |
| 6,461,607 B1 | 10/2002 | Farmer | |
| 6,696,057 B1 | 2/2004 | Bojrab | |
| 6,962,779 B1 | 11/2005 | Macina | |
| 7,244,424 B2 | 7/2007 | Mikelsaar et al. | |
| 7,374,753 B1 | 5/2008 | Farmer et al. | |
| 9,168,275 B2 | 10/2015 | Finegold | |
| 2001/0036453 A1 | 11/2001 | Reid et al. | |
| 2004/0028689 A1 | 2/2004 | Borody | |
| 2004/0062757 A1 | 4/2004 | Finegold | |
| 2004/0167062 A1 | 8/2004 | Bolte | |
| 2004/0170617 A1 | 9/2004 | Finegold | |
| 2012/0252775 A1* | 10/2012 | Finegold | A61K 31/397 514/210.06 |

OTHER PUBLICATIONS

Bailey K. Ciannelli L. et al. Comparative Analysis of Marine Ecosystems: workshop on predator—prey interactions. Biol. Lett. 2010; 6, 579-581—Exhibit 3.

Chao Anne, Bunge John. Estimating the number of species in a stochastic abundance model Biometrics 2002: 58:531-539—Exhibit 4.

Dowd S. Wolcott R et al. Polymicrobial nature of chronic diabetic foot ulcer biofilm infections determined using bacterial tag encoded FLX amplicon pyrosequencing (bTEFAP). Dowd Laboratory. PLoS ONE 3, e3326, 2008—Exhibit 5.

Dowd et al. Bacterial tag-encoded FLX amplicon pyrosequencing (bTEFAP for microbiome studies: Bacterial diversity in the Ileum of newly weaned *Salmonella*-infected pigs. Foodborne Pathog. Dis, 5. 459-472, 2008—Exhibit 6.

Dowd et al. Evaluation of the bacterial diversity in the feces of cattle using 16S rDNA bacterial tag-encoded FLX amplicon pyrosequencing (bTEFAP). BMC microbial. 8, 125, 2008—Exhibit 7.

Emanuele E, Orsi P, Boso M et al. Low-grade endotoxemia in patients with severe autism, *Neurosci Lett* 2010; 471(3):162-165,—Exhibit 8.

Finegold SM. Molitoris D. Song Y et al. Gastrointestinal microflors studies in late-onset autism. Clin Infect Dis 2002;35 (Suppl. 1):S6-S16—Exhibit 9.

Finegold SM, Dowd SR, Gontcharova V et al. Pyrosequencing study of fecal microflora of autistic and control children. *Anaerobe* 2010; 16:444-453.—Exhibit 10.

Finegold SM. Therapy and epidemiology of autism-clostridial spores as key elements. Med Hypotheses 2008;70(3):508-511—Exhibit 11.

Finegold SM, Molitoris D. Vaisanen ML. Study of the in Vitro Activities of Rifaximin and Comparator Agents against 536 Anaerobic Intestinal Bacteria from the Perspective of Potential Utility in Pathology Involving Bowel Flora. Antimicrob Agents Chemother 2009: 53(1):281-286—Exhibit 12.

(Continued)

*Primary Examiner* — Yong S. Chong

(74) *Attorney, Agent, or Firm* — Adriano & Associates

(57) ABSTRACT

The invention provides for methods of treating autism associated with *Desulfovibrio* overgrowth in the gastrointestinal tract of a patient, said method comprising administering to the patient suffering from said autism a treatment course of aztreonam in an amount effective to treat autism in the patient, thereby treating autism.

11 Claims, 9 Drawing Sheets

Specification includes a Sequence Listing.

(56) References Cited

OTHER PUBLICATIONS

Finegold SM. Bolanos M, Sumannen PH, Molitoris DR. In Vitro Activities of Televascin and Six Comparator Agents against Anaerobic Bacterial Isolates. *Antimicrob Agents Chemther* 2009; 53(9):3996-4001—Exhibit 13.

Herbert MR, Russo JP, Yang S et al. Autism and environmental genomics. Neurotoxicology 2006;27(5):671-684—Exhibit 14.

James SJ, Cutler P, Melnyk S et al. Metabolic biomarkers of increased oxidative stress and impaired methylation capacity in children with autism. *Am J Clin Nutr* 2004:80(6):1611-1617—Exhibit 15.

MacFabe DF, Cain DP, Rodriguez-Capote K et al. Neurobiological effects of intraventricular propionic acid in rats: possible role of short chain fatty acids on the pathogenesis and characteristics of autism spectrum disorders. *Behav Brain Res* 2007; 176(1):149-169—Exhibit 16.

McCartney S, Ballinger A, et al. Endothelin in human inflammatory bowel disease: comparison to rat trinitrobenzenesulphonic acid-induced colitis. Life Sci. 2002, (71)1893-1904—Exhibit 17.

Marquet P, Duncan SH, Chassard C. Bernaller-Donadilie A, Flint HJ. Lactate has the potential to promote hydrogen sulphide formation in the human colon. FEMS *Microbiol Lett* 2009; 299(2):128-134—Exhibit 18.

Martin et al. Metallopeptidase inhibitors of tetanus toxin: A combinatorial approach, J. Med. Chem., 1999, 42(3):515-525.—Exhibit 19.

Martinez V, Dowd S. Sun Y, Alien V. Tag-encoded pyrosequencing analysis of bacterial diversity in a single soil type as affected by management and land use. *Soil. Biol. Biochem* 2008; 40:2752-2770—Exhibit 20.

Parracho HM, Bingham MO, Gibson GR, McCartney AL. Differences between the gut microflora of children with autistic spectrum disorders and that of healthy children. J Med Microbiol 2005;54(Pt 10):987-991—Exhibit 21.

Pochini L, Gailoccio M, Scumaci D et al. Interaction of beta-lactam antibiotics with the mitochondrial carnitine/acylcarnitine transporter. *Chem Biol Interact* 2008; 173(3):187-194—Exhibit 22.

Ramesh et al. Prevention of clostridium difficile-induced ileocecitis with bacteriophage. Anaerobe 1999, 5:59-78,—Exhibit 23.

Rimland B. The autism epidemic, vaccinations, and mercury. *J Nutr Environ Med* 2000; 10:261-266—Exhibit 24.

Sandler RH, Finegold SM, Bolte ER et al. Short-term benefit from oral vancomycin treatment of regressive-onset autism. J Child Neurol 2000; 15(7):429-435—Exhibit 25.

Shapiro RL, Hatheway C. Swerdlow DL. Botulism in the United States: A clinical and epidemiological review. *Ann Intern Med* 1998; 129(3)221-228—Exhibit 26.

Song Y, Liu C, Finegold SM. Development of a Flow Chart for Identification of Gram-Positive Anaerobic Cocci in the Clinical Laboratory. Appl Environ Microbiol 2006;45(2):512-516—Exhibit 27.

Song Y, Liu C, Finegold SM. Real-time PCR quantitation of clostridia in feces of autistic children. Appl Environ Microbiol 2004;70(11):6459-6465—Exhibit 28.

Suchodolski et al. The effect of the macrodile antiobiotic tylosin on microbial diversity in the canine small intestine as demonstrated by massive parallel 16S cRNA gene sequencing. *Porphyromonas bennonis* sp.nov., isolated from human clinical specimens. *Int BMC Microbiol* 2009; 9:210—Exhibit 29.

Summanen PH, Lawson PA, Finegold SM. *Porphyromonas bennonis* sp.nov., isolated from human clinical specimens. *Int J Syst Evol Microbiol* 2009; 59:1727-1732—Exhibit 30.

Waring RH, Klovrza LV. Sulphur metabolism in autism. J Nutr Environ Med 2000; 10:25-32—Exhibit 31.

Weglarz L, Wawszczyk J. Orchel A. Jaworska-Kik M, Dzierzewicz Z. Phytic acid modulates in vitro IL-8 and IL-6 release from colonic epithelial cells stimulated with LPS and IL-1 beta. Dig Dis Sci 2007; 52(1):93-102—Exhibit 32.

Wexler H, Reeves D, Summanen H, et al. *Sutterella wadswothensis* gen. nov., sp. Nov., bite resistant microaerophilic campylobacter gracilis-like clinical isolates Int. *J Syst Bacteriol* 1996; 46:252-258—Exhibit 33.

Wexler H, Molitoris E. et al. Comparison of spiral gradient endpoint and agar dilution methods for susceptibility testing of anaerobic bacteria: a multilaboratory collaborative evaluation. Int. *J Clin Microbiol* 1996; 34:170-174—Exhibit 34.

Wolcott R, Gontcharova V, Sun Y, Dowd S. Evaluation of the bacterial diversity among individual venous leg ulcers using bacterial tag-encoded FLX and titanium amplicon pyrosequencing and metagenomics approaches. Int. *BMC Bacteriol* 2009; 9, 226—Exhibit 35.

Sandler et al., Pediatric Research, 1998; 43:105-105 (abstract) Exhibit 51 (provided herein).

Sullivan et al., Journal of Internal Medicine, 2005, 257:78-92 Exhibit 52 (provided herein).

http://www.neurologychannel.com/autism/treatment.shtml Exhibit 53 (provided herein).

http://www.mayoclinic.com/health/DS00348/DSECTION=treatments%2Dand%2Ddrugs Exhibit 54 (provided herein).

\* cited by examiner

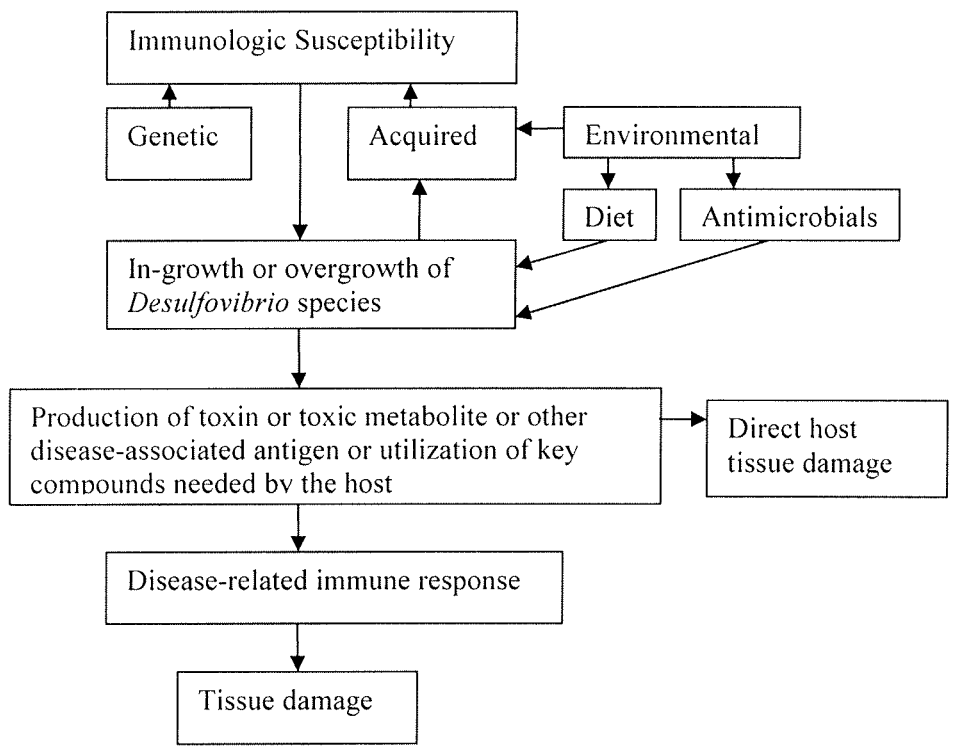
Figure 5. Hypothetical pathogenesis of autism

SEQUENCE LISTING

```
<160> NUMBER OF SEQ ID NOS: 21

<210> SEQ ID NO 1
<211> LENGTH: 20
<212> TYPE: DNA
<213> ORGANISM: Artificial Sequence
<220> FEATURE:
<223> OTHER INFORMATION: D. desulfuricans forward primer

<400> SEQUENCE: 1
ggatcgtaaa cctctgtcag                                                    20

<210> SEQ ID NO 2
<211> LENGTH: 19
<212> TYPE: DNA
<213> ORGANISM: Artificial Sequence
<220> FEATURE:
<223> OTHER INFORMATION: D. desulfuricans reverse primer

<400> SEQUENCE: 2
ctttacgccc agtgattcc                                                     19

<210> SEQ ID NO 3
<211> LENGTH: 19
<212> TYPE: DNA
<213> ORGANISM: Artificial Sequence
<220> FEATURE:
<223> OTHER INFORMATION: D. desulfuricans reverse primer

<400> SEQUENCE: 3
ctttacgccc agtaattcc                                                     19

<210> SEQ ID NO 4
<211> LENGTH: 26
<212> TYPE: DNA
<213> ORGANISM: Artificial Sequence
<220> FEATURE:
<223> OTHER INFORMATION: D. desulfuricans probe

<400> SEQUENCE: 4
aactacgttg tgctaatcag cagcgt                                             26
```

<210> SEQ ID NO 5
<211> LENGTH: 20
<212> TYPE: DNA
<213> ORGANISM: Artificial Sequence
<220> FEATURE:
<223> OTHER INFORMATION: D. fairfieldensis forward primer

<400> SEQUENCE: 5
ggactcatcc tcatacgaca                                              20

<210> SEQ ID NO 6
<211> LENGTH: 17
<212> TYPE: DNA
<213> ORGANISM: Artificial Sequence
<220> FEATURE:
<223> OTHER INFORMATION: D. fairfieldensis reverse primer

<400> SEQUENCE: 6
tcgagtagag tggcgca                                                 17

<210> SEQ ID NO 7
<211> LENGTH: 24
<212> TYPE: DNA
<213> ORGANISM: Artificial Sequence
<220> FEATURE:
<223> OTHER INFORMATION: D. fairfieldensis probe

<400> SEQUENCE: 7
gcaagcagag gccgtctttc ccct                                         24

<210> SEQ ID NO 8
<211> LENGTH: 20
<212> TYPE: DNA
<213> ORGANISM: Artificial Sequence
<220> FEATURE:
<223> OTHER INFORMATION: D. intestinalis forward primer

<400> SEQUENCE: 8
ggatcgtaaa cctctgtcag                                              20

<210> SEQ ID NO 9
<211> LENGTH: 19
<212> TYPE: DNA
<213> ORGANISM: Artificial Sequence
<220> FEATURE:
<223> OTHER INFORMATION: D. intestinalis reverse primer

<400> SEQUENCE: 9
ctttacgccc agtgattcc                                               19

<210> SEQ ID NO 10
<211> LENGTH: 19
<212> TYPE: DNA
<213> ORGANISM: Artificial Sequence
<220> FEATURE:
<223> OTHER INFORMATION: D. intestinalis reverse primer

<400> SEQUENCE: 10
ctttacgccc agtaattcc                                               19

<210> SEQ ID NO 11
<211> LENGTH: 25
<212> TYPE: DNA
<213> ORGANISM: Artificial Sequence
<220> FEATURE:
<223> OTHER INFORMATION: D. intestinalis probe

```
<400> SEQUENCE: 11
agaaaccgca ccgtgctaat cagcg                                              25

<210> SEQ ID NO 12
<211> LENGTH: 20
<212> TYPE: DNA
<213> ORGANISM: Artificial Sequence
<220> FEATURE:
<223> OTHER INFORMATION: D. piger forward primer

<400> SEQUENCE: 12
ggatcgtaaa cctctgtcag                                                    20

<210> SEQ ID NO 13
<211> LENGTH: 19
<212> TYPE: DNA
<213> ORGANISM: Artificial Sequence
<220> FEATURE:
<223> OTHER INFORMATION: D. piger reverse primer

<400> SEQUENCE: 13
ctttacgccc agtgattcc                                                     19

<210> SEQ ID NO 14
<211> LENGTH: 19
<212> TYPE: DNA
<213> ORGANISM: Artificial Sequence
<220> FEATURE:
<223> OTHER INFORMATION: D. piger reverse primer

<400> SEQUENCE: 14
ctttacgccc agtaattcc                                                     19

<210> SEQ ID NO 15
<211> LENGTH: 29
<212> TYPE: DNA
<213> ORGANISM: Artificial Sequence
<220> FEATURE:
<223> OTHER INFORMATION: D. piger probe

<400> SEQUENCE: 15
aagaaactag ggtgttctaa tcatcatcc                                          29

<210> SEQ ID NO 16
<211> LENGTH: 20
<212> TYPE: DNA
<213> ORGANISM: Artificial Sequence
<220> FEATURE:
<223> OTHER INFORMATION: D. vulgaris forward primer

<400> SEQUENCE: 16
ggatcgtaaa cctctgtcag                                                    20

<210> SEQ ID NO 17
<211> LENGTH: 19
<212> TYPE: DNA
<213> ORGANISM: Artificial Sequence
<220> FEATURE:
<223> OTHER INFORMATION: D. vulgaris reverse primer

<400> SEQUENCE: 17
ctttacgccc agtgattcc                                                     19

<210> SEQ ID NO 18
```

```
<211> LENGTH: 19
<212> TYPE: DNA
<213> ORGANISM: Artificial Sequence
<220> FEATURE:
<223> OTHER INFORMATION: D. vulgaris reverse primer

<400> SEQUENCE: 18
ctttacgccc agtaattcc                                              19

<210> SEQ ID NO 19
<211> LENGTH: 23
<212> TYPE: DNA
<213> ORGANISM: Artificial Sequence
<220> FEATURE:
<223> OTHER INFORMATION: D. vulgaris probe

<400> SEQUENCE: 19
cggtgctaat cagccgtggt ctg                                         23

<210> SEQ ID NO 20
<211> LENGTH: 25
<212> TYPE: DNA
<213> ORGANISM: Artificial Sequence
<220> FEATURE:
<223> OTHER INFORMATION: Desulfovibrio spp. forward primer

<400> SEQUENCE: 20
ccgtagatat ctggaggaac atcag                                       25

<210> SEQ ID NO 21
<211> LENGTH: 25
<212> TYPE: DNA
<213> ORGANISM: Artificial Sequence
<220> FEATURE:
<223> OTHER INFORMATION: Desulfovibrio spp. reverse primer

<400> SEQUENCE: 21
acatctagca tccatcgttt acagc                                       25
```

METHOD FOR DIAGNOSING, PREVENTING, AND TREATING NEUROLOGICAL DISEASES

This patent application is a divisional application of U.S. Ser. No. 13/117,073, filed on May 26, 2011, which claims the benefit of U.S. Ser. No. 61/275,714, filed May 26, 2010, the contents of all of which are herein incorporated by reference in their entireties into the present patent application.

Throughout this application various publications are referenced. The disclosures of these publications in their entireties are hereby incorporated by reference into this application in order to more fully describe the state of the art to which this invention pertains.

FIELD OF THE INVENTION

The present invention relates to treatment of neurological diseases, especially autism. The treatment involves antibiotics and repopulating the gastrointestinal tract with normal flora and also vaccines and bacteriophage.

BACKGROUND OF THE INVENTION

The composition of the normal gastrointestinal flora varies somewhat from individual to individual. Some bacterial species may be carried only transiently, but most are fairly permanent. Some members of the normal flora can become pathogenic if they acquire additional virulence factors (e.g., *E. coli*) or are introduced into normally sterile sites (e.g., *Staphylococcus aureus*). Normal flora is generally beneficial—for example, the normal flora may prevent pathogenic microorganisms from proliferating in the body (a phenomenon known as colonization resistance), and may also produce essential nutrients (e.g., vitamin K is produced by the gut flora).

The use of antibiotics is ubiquitous among children and adults for bacterial infections, and they are often also prescribed for viral infections. This prolific use has come under criticism for various reasons, most notably for inducing microbial resistance to previously effective antibiotics and rendering them less effective or ineffective against dangerous human pathogens. For example, multidrug-resistant strains of *Mycobacterium tuberculosis* seriously threaten tuberculosis (TB) control and prevention efforts. Administration of broad-spectrum antibiotics has a profound effect on the normal flora and can result in colonization with antibiotic-resistant organisms. Antibiotic-mediated disruption of the normal flora can lead to fungal infections, such as invasive candidiasis, or to antibiotic-associated colitis caused by *Clostridium difficile*.

Several neurological or neuropsychiatric conditions, such as autism may have gastrointestinal etiology. Published data lend credence to the notion that an alteration in bowel microflora may be associated with autistic symptoms (Sandler et al., *J. Child Neurol.* 15, 429-435, 2000; Finegold et al., *Clin. Infect. Dis.* 35 (Suppl. 1), S6-S16, 2002; Song et al., *Appl. Environ. Microbiol.* 70, 6459-6465, 2004; Parracho et al., *J. Med. Microbiol.* 54, 987-991, 2005; Finegold et al., *Medical Hypotheses* 70, 508-511).

SUMMARY OF THE INVENTION

The invention relates to methods for preventing or treating a gastrointestinal or neurological disorder. The disorders preferably have as an etiological component a microbial agent. The method comprises administering to the patient an antimicrobial composition in an amount effective to inhibit or eliminate the microbial agent. By "microbial agent" is meant a microbe or its toxin. Disorders that can be treated by the methods of the invention include attention deficit disorder, depression, bipolar disorder, juvenile diabetes, primary sclerosing cholangitis, Alzheimer's disease, Parkinson's disease, Whipple's disease, Tourette's syndrome, juvenile rheumatoid arthritis, adult rheumatoid arthritis, multiple sclerosis, Asperger's syndrome, pervasive development disorder, autism (especially early onset and regressive autism), Rhett's syndrome, D-lactic acidosis, obesity, atherosclerosis and atherosclerotic heart disease, chronic fatigue syndrome, Gulf War illness, post-traumatic stress disorder and schizophrenia. Gastrointestinal disorders can include antimicrobial associated diarrhea or inflammatory bowel diseases such as ulcerative colitis or Crohn's disease. The method can be used where the agent is a species of the genus *Clostridium* or *Desulfovibrio* or other genera that are abnormal in the intestinal flora. Colon cancer may also be related to the presence of such organisms in the bowel and so may be prevented by eliminating such organisms. As used herein, "abnormal" refers to organisms that 1) are not normally present in the intestinal flora; 2) are present in significantly higher or lower concentrations than in the normal flora; 3) produce one or more toxic products not produced by organisms of the normal flora; 4) compete with the host for essential nutrients or other elements; and/or 5) produce disease in people with abnormal immune system.

The antimicrobial composition preferably has at least one of the following properties: oral palatability, sustained concentration in the gastrointestinal tract, low absorption from the gut (and hence low systemic concentration), higher activity against the abnormal organism relative to activity against other normal gut flora, bactericidal activity, not cross-resistant with vancomycin or other antimicrobials that are important for treatment of systemic infections, resistance does not develop readily, the composition is well tolerated orally and over an extended period of time (preferably at least 3-4 months), it is effective when given once or twice daily, has low systemic and gastrointestinal toxicity, and is economical. Available in liquid form for subjects unable to swallow pills or tablets.

An alternative or supplemental therapy involves the use of a bacteriophage in addition to or as the antimicrobial composition. The bacteriophage is preferably specific for the abnormal organism.

Another alternative or supplemental method of treating a neurological or gastrointestinal disorder is a therapy regimen to repopulate the gastrointestinal tract with normal flora. This therapy comprises administering to the patient at least one of the normal gut inhabitants that is present in healthy people in high numbers by any route. This method can be used in conjunction with the antimicrobial composition. Preferably, the antimicrobial is first administered to suppress or eradicate the abnormal organism, then the normal flora is repopulated by the administration of at least one of the normal gut inhabitants. It is preferred that the antimicrobial treatment is complete before the administration of the at least one of the normal gut inhabitants.

In another embodiment, the invention includes a method of detecting a neurological or gastrointestinal disorder that has as an etiological component an abnormal microorganism in the intestinal flora. The method comprises collecting a gastrointestinal sample from a patient suspected of having such disorder, and screening for the presence or concentration of the abnormal organism and/or certain toxic substances. This method can be used with other techniques to diagnose the presence of autism in a patient, such as observation of lack of eye contact, difficulty with social relationships, speech delays, or odd physical behaviors. Screening instruments have been developed to quickly gather information about a child's social and communicative development within medical settings. Current diagnosis relies on checklists of symptom which include the Checklist of Autism in Toddlers (CHAT), modified Checklist for Autism in Toddlers (M-CHAT), the Screening Tool for Autism in Two-Year-Olds (STAT), and the Social Communication Questionnaire (SCQ, for children 4 years of age and older).

Alternatively, if the abnormal organism produces a toxin, the sample can be screened with an antibody directed against a conserved epitope of the toxin, where a specific interaction of the antibody with the sample indicates the presence of a neurological disorder in the patient. An alternative embodiment is the use of an antibody generated against the specific toxin causing the neurological or gastrointestinal disorder. Such an antibody can be produced by conventional means (e.g., polyclonal, monoclonal), or can be derived from a patient having a high serum titer to the causative agent.

Another feature of the invention is a method of treating or preventing a neurological or gastrointestinal disorder in a patient, the disorder having as an etiological component a microbe that produces a toxin, the method comprising vaccinating the patient with an antigenic epitope of the toxin such that an immune response capable of interaction with gut flora (e.g., via Peyer's patches, IgA, or other, immunoglobulin or complement activation local to the gut) can be elicited upon antigen challenge from microbe proliferation in the gut.

The invention also provides for methods for treating autism associated with *Desulfovibrio* overgrowth in the gastrointestinal tract of a patient, said method comprising administering to the patient suffering from said autism a treatment course of aztreonam in an amount effective to treat autism in the patient, thereby treating autism.

The invention further provides for methods for screening for compounds that inhibit *Desulfovibrio* and thereby inhibit autism, wherein said method comprises obtaining a sample from a subject, contacting a sample containing *Desulfovibrio* with a molecule of interest, and determining whether contact results in inhibition of *Desulfovibrio*.

The invention further provides for methods of screening for autism comprising obtaining a sample from a subject, and determining whether *Desulfovibrio* is present in the sample, the presence of *Desulfovibrio* being indicative of autism.

BRIEF DESCRIPTION OF THE DRAWINGS

FIG. 2 is a graph of the Principal Component Analysis at the phylum level.

FIG. 3 is graph of the Principal Component Analysis at the genus level.

FIG. 5 shows a diagram of the proposed pathogenesis of autism.

DETAILED DESCRIPTION OF THE INVENTION

Figure 1A:
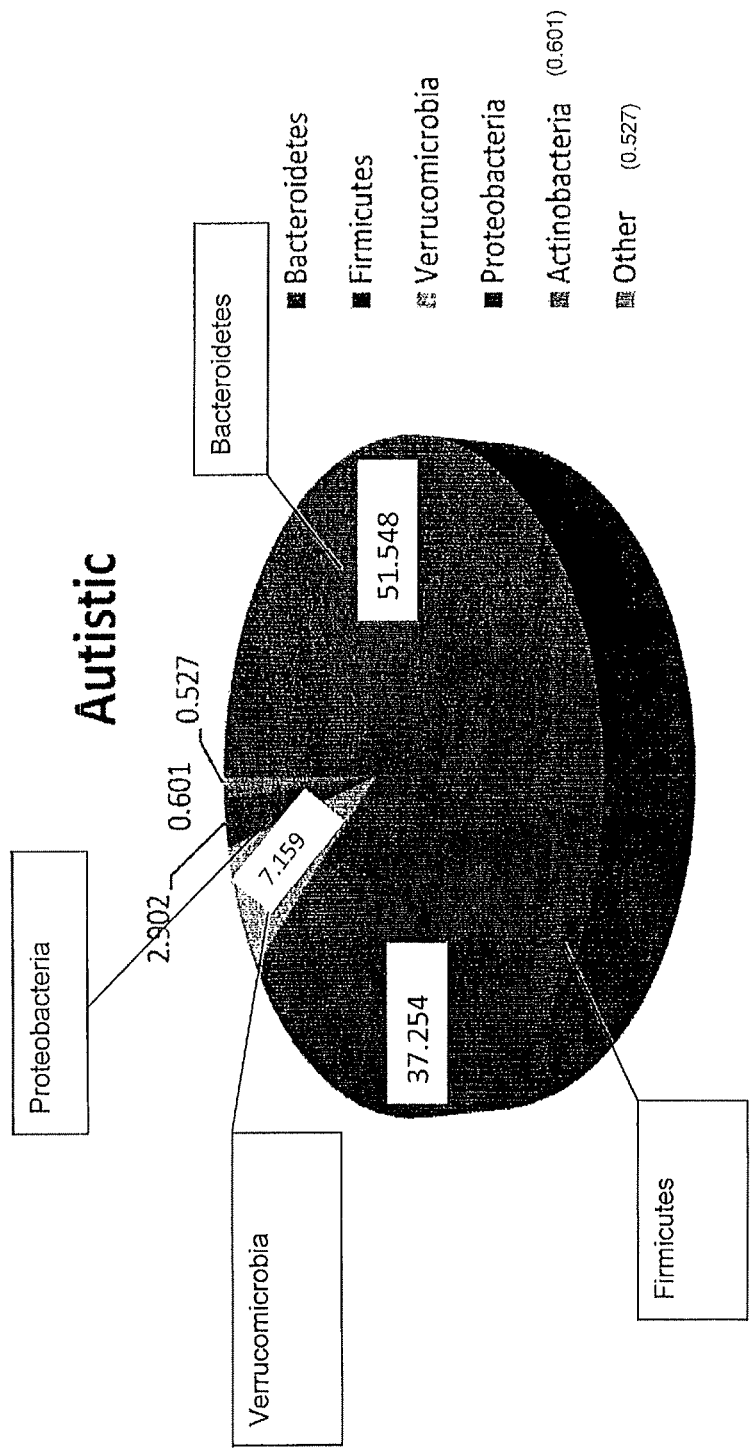
FIG. 1 is a pie chart showing the frequencies of bacterial phyla in the stool of autistic children (FIG. 1A), control children (FIG. 1B) and siblings of autistic children (FIG. 1C).

The invention provides methods for treating autism associated with *Desulfovibrio* overgrowth in the gastrointestinal tract of a patient. The method comprises administering a treatment course of aztreonam in an amount effective to treat autism in the patient. In a further embodiment, the method comprises administering a beta-lactamase inhibitor selected from clavulanic acid, tazobactam, sulbactam and LK-157 or others.

In one embodiment, the aztreonam and the beta-lactamase inhibitor are administered concurrently.

In another embodiment, the invention further comprise administering a probiotic and/or a probiotic group. Examples of probiotic includes but not limited to bacteria (a single or multiple species) that competes with *Desulfovibrio* for nutrients and bacteria that inhibits growth of *Desulfovibrio*. A more detailed description is found in the section "Probiotic Therapy".

In another embodiment, the subject (or patient) is selected from human, monkey, ape, dog, cat, cow, horse, rabbit, mouse and rat subjects. In a further embodiment, the subject is human.

It has been discovered that disruption of gastrointestinal flora or poorly developed gastrointestinal flora in young infants and subsequent pathogenic microbial proliferation in one or more regions of the gastrointestinal tract can mediate a variety of disruptions of neurological function. These neurological disruptions are mediated by toxins, or profound metabolic disturbances related to the metabolism of the offending organism (e.g. sulfate metabolism problems related to the utilization of sulfate by *Desulfovibrio*) which extends to disrupting the protective mucin layer of the GI tract which is made up of sulfated glycoprotein which can result in inflammation and increased permeability of the gut particularly neurotoxins, produced by one or more species of the proliferating microbes. Bacteria of several genera are indicated as the likely causative agents and/or their toxins. The toxins can be potent, non-necrotizing neurotoxins that disrupt neurotransmitter release. Neurotoxins such as the neuromuscular transmission inhibitor tetanospasmin, produced by *C. tetani*, have traditionally been considered to be dangerous following systemic exposure only (e.g., exposure by introduction of the bacterium or spores into a wound, for example). It has also been discovered that patients of certain neurological condition have an intestinal flora that is different from the normal flora. As a specific example, when compared to the normal flora, the intestinal flora of autistic patients contains a significantly greater percentages (based on the total flora) of *Desulfovibrio*. As such, the presence of an abnormal *Desulfovibrio* concentration can be indicative of autism.

It has also been discovered that the methods of the invention, including antibiotic therapy directed to the abnormal microorganism, results in improved neurological function through inhibition or elimination of the proliferating species. Recurrence of the neurological symptoms can be limited or prevented by repopulation of the gastrointestinal tract by normal human gut flora ("probiotic therapy" or fecal transplantation) or by administration of certain foodstuffs to stimulate growth of the desirable bacteria ("prebiotic therapy"). The neurological symptoms themselves can be prevented or limited in the place by appropriate probiotic or prebiotic therapy following administration of wide spectrum antibiotics, especially in children or compromised adults. Alternatively, limiting the use of broad-spectrum antibiotics can also help prevent the widespread disruption of the gastrointestinal flora at the outset. Finally, vaccination leading to a gut level immunoresponse against toxin antigens responsible for the neurologic symptoms can be used to prevent occurrence of disorders due to microbial overgrowth.

The pathogenic proliferation of microbes in the gut can at least partially cause deleterious neurological symptoms and syndromes of many disorders, including at least some forms of pervasive development disorder including autism (both early-onset and late-onset autism); Asperger's syndrome; attention deficit disorder; depression; bipolar disorder; Alzheimer's disease; Parkinson's disease; Whipple's disease; Tourette's syndrome; Rhett's syndrome; and schizophrenia.

Additional diseases and disorders are also caused by disrupted gut microbial flora, and can be treated and/or prevented by antibiotic and probiotic or prebiotic measures. Examples of such disorders include antimicrobial-associated diarrhea and inflammatory bowel disease (including, for example, ulcerative colitis and Crohn's disease). A very important example is hospital-acquired (nosocomial) systemic infection due to *S. aureus, Pseudomonas, Klebsiella-Enterobacteria*, etc. which may often be traced to previous colonization of the intestinal tract by these organisms following hospitalization.

Many, if not most, of the disorders mentioned above are clearly unrelated by conventional medical knowledge and/or standards. However, the surprising discovery of a common etiology makes possible a common diagnostic, therapeutic, and preventative concept, embodied in the methods of the invention.

Abnormal Microorganism

The present invention targets members of several genera as causative or contributing to the neurological or intestinal disease. The genera, including *Clostridium, Desulfovibrio, Bacteroides, Turicibacter, Weissella, Parabacteroides*, and *Ruminoccocus. Clostridium* are plausible as agents of these neurological disorders, because several members of this genus are known to produce neurotoxins, they proliferate enterically during antimicrobial therapy (e.g., *C. difficile*), and they have been implicated in diarrheal diseases of humans and animals. For example, *Clostridium tetani* is the bacterium that causes tetanus (lockjaw) in humans. *C. tetani* spores can be acquired from soil or any type of skin trauma involving an infected device. If an anaerobic environment is present, the spores will germinate and eventually form active *C. tetani* cells. At the tissue level, the bacterium then releases an exotoxin called tetanospasmin that causes certain nervous system irregularities by means of retrograde transmission through neurons to the nervous system. One of the toxin's classic effects includes constant skeletal muscle contraction due to a blockage of inhibitory interneurons that regulate muscle contraction. Prolonged systemic infection eventually leads to respiratory failure, among other things. If not treated early, the mortality rate of this disease is high. Botulism is another disease related to clostridia (*C. botulinum*) and infant botulism is caused by GI colonization with this organism acquired from food or soil and can be precipitated or exacerbated by antibiotic therapy.

*Desulfovibrio* is a gram negative, rod shaped, sulfate reducing bacterium, which is an anaerobe and which may compete with the host for sulfur. Its metal corroding ability has led to numerous health and safety concerns; and its production of $H_2S$ and endotoxin can lead to genotoxic and other toxic-related problems.

Although several genera, as exemplified above, are generally culprits in the gastrointestinal component of neurological disorders, other abnormal organisms may also be involved. The other abnormal organisms, however, and their association with specific diseases/conditions can be elucidated using the methods described in this document.

Recognition of the gastrointestinal component of these neurological disorders allows diagnosis and treatment of a novel and specific nature.

Diagnosis

The invention also provides methods for screening for compounds that inhibit *Desulfovibrio* and thereby inhibit autism. Method for screening for compounds comprises obtaining a sample from a subject, contacting a sample containing *Desulfovibrio* with a molecule of interest, and determining whether contact results in inhibition of *Desulfovibrio*.

In one embodiment, the inhibition of *Desulfovibrio* includes decreasing growth of *Desulfovibrio*, eliminating growth of *Desulfovibrio* or delaying growth of *Desulfovibrio*.

In one embodiment, the compound is bacteriostatic or bactericidal. In another embodiment, the compound is a small molecule, protein, peptide, antibiotic, pre-formed antibodies, bacteriophage or a combination thereof.

In one embodiment, the screening method comprises separately contacting each of a plurality of samples to be tested. In another embodiment, the plurality of samples comprises more than about $10^4$ samples. In a further embodiment, the plurality of samples comprises more than about $5 \times 10^4$ samples.

In another embodiment, the sample is selected from feces, urine, blood and plasma.

The invention further provides a method of screening for autism comprising obtaining a sample from a subject, and determining whether *Desulfovibrio* is present in the sample, the presence of *Desulfovibrio* being indicative of autism.

Diagnostic options include tests based on detection of the organism itself (culture or PCR), the gene that codes for the toxin produced by the overgrown microbe, the toxin itself, or proliferation of a particular toxin-producing microbe. Such tests include amplification of nucleic acids encoding the toxin (e.g., by PCR, using primers/probes specific for the toxin or toxins of interest; specific hybridization assays (e.g., in situ hybridization; Northern, Southern, or dot blots; microarray hybridization, etc.); detection of the toxin itself using, e.g., anti-toxin antibodies, (generated monoclonally, polyclonally, or derived from patients with high titers of anti-toxin antibodies (such antibodies are likely to be better reagents than commercial tetanus antibodies or antibodies generated against conserved regions of multiple bacteria, since they will be exceptionally specific for the causative toxin) in ELISAs, sandwich assays, Western blots, or affinity chromatography; animal assays; laser mass spectroscopy, or any other methods known to those of skill in the art. Samples can be obtained from fecal samples, blood, plasma, urine, saliva, cerebrospinal fluid, biopsy tissue, or any other patient source, and may be directly tested or after isolation of suspected causative agents.

Screening assays are based on detection of suspect organisms in the feces of patients using culture (sometimes employing enrichment, selective and/or differential media) and microbiologic and molecular identification techniques, including immunofluorescent techniques, genetic probes, laser mass spectroscopy, or other methods known in the art.

The methods of diagnosis herein can be used in conjunction with or to supplement other diagnostic methods known in the art. For example, diagnosis for autism may include interviews with parents/caretaker of the patient or observation of the patient.

Selection of Antimicrobial Therapeutic Agents
Antimicrobials to Treat Disorders Resulting from Disrupted Gut Flora Once a positive diagnosis has been made, antimicrobial therapy can be started to inhibit or eliminate the microbe whose enteric overgrowth and/or toxin production is causing the disorder. The antimicrobials used to treat the disorders described above should have certain characteristics for optimal benefit and minimal side effects. Certain antimicrobials have characteristics appropriate to treat even very young children, and such drugs are useful to treat disorders having the gut-brain involvement. Preferably, an antimicrobial selected as a therapy for any of the above disorders will have one or more of the following properties:

1. Good in vitro activity against most or all clostridial species and/or *Desulfovibrio*;
2. Relatively poor activity against most other organisms normally found in the gut flora;
3. Safe doses capable of achieving a concentration in the colon or elsewhere in the GI tract where the offending organism proliferates exceeding the minimal inhibitory concentration or minimal bactericidal concentration of the drug by at least four or five-fold concentrations;
4. Preferably absorbed very little or not at all when given orally (to minimize systemic effects);
5. Bactericidal activity preferred (rather than purely inhibitory activity);
6. Not cross-resistant with vancomycin or other drugs that are important for treatment of systemic infections;
7. Resistance doesn't develop readily: (i.e., the drug doesn't readily engender resistance in bacteria);
8. Palatable in liquid form when taken orally (for administration to children), or readily formulated into other oral doses (to enhance patient compliance);
9. Well tolerated orally over extended period of time (preferably at least 3-4 months);
10. Little or no toxicity, either systemically or in the bowel;
11. Preferably effective when given only once or twice daily; and
12. Preferably moderate in price.

Drugs that have one or more of the above characteristics may have utility for antimicrobial therapy in treating neurological disorders with a gut flora etiology include those listed below:

ABT-773 Polymyxin
Aminoglycosides Pristinamycin
Ampicillin/sulbactam Ramoplanin
 Rifaximin
Amphomycin Ristocetin
Azithromycin Rosamicin, rosaramicin
Aztreonam
Bacitracin Spectinomycin
Beta-lactamase inhibitors
Carbomycin Spiramycin
Cephalosporins, oral Staphylomycin
Clarithromycin Streptogramin
Colistin
Erythromycins Synergistin
Fidaxomycin (OPT 80)
Furazolidone, other nitrofurans Teicoplanin
Fusidic acid, Na fusidate Telavancin
 Telithromycin
Gramicidin Ticarcillin/clavulanic acid
Imipenem, oral; other penems Tyrocidin
Josamycin Tyrothricin
Linezolid, other oxazolidinones Vancomycin
Macrolides Vernamycin
Metronidazole, other nitroimidazoles Virginiamycin
Mikamycin
Novobiocin
Oleandomycin,
triacetyloleandomycin
Ostreogrycin
Piperacillin/tazobactam Appropriate doses of these antimicrobials are within the range given for many other conditions for which the antimicrobials are prescribed. Dosage information can be found, for example, in the Physicians' Desk Reference, 54th Edition, Medical Economics Company, Montvale, N.J. (2000). In certain instances, the doses may be elevated to the extent necessary to maintain a bactericidal or bacteriostatic concentration throughout the gastrointestinal tract. The antimicrobials are preferably formulated for oral administration, such as in liquid form, tablet, capsule, granules, chewable, etc. Tablets or capsules may be enterically coated to minimize gastric absorption of the drug (since very few bacteria are capable of colonizing the stomach, this is not necessarily a primary target of the therapies of the invention). However, when the pH of the stomach is high or emptying is slow due to certain drugs or diseases, the stomach can be colonized with many bacteria.

The antimicrobials can be administered as known in the art. It is desirable to select a route of administration that is most effective for the therapy, examples thereof being oral administration or parenteral administration such as intravenous administration.

A preferred compound for treating *Clostridium* overgrowth in the gut is ramoplanin, also known as A-16686 (see, e.g., U.S. Pat. Nos. 4,303,646; 4,328,316; 4,427,656; 5,539,087; and 5,925,550; and Parenti et al.; *Drugs Exp Clin Res* 16(9):451-5 (1990); all herein incorporated by reference). This antibiotic is not cross-resistant with vancomycin, it engenders very little to no resistance in bacteria, is not detectably absorbed systemically in humans (making it exceptionally safe, even for young children), can be made palatable in a liquid form, achieves high concentrations in the large intestine, has very good activity against clostridia, can be given twice a day, and is primarily active against gram positive organisms at the dosage levels administered. Ramoplanin is preferable to drugs such as vancomycin and metronidazole, which have previously been used, because, for example, vancomycin, while achieving a high concentration in the intestines throughout, is effective against Bacteroides, a beneficial genus of gut flora, as well as clostridial species. It is also a potent antibiotic against, e.g., systemic methicillin-resistant *Staphylococcus* infections, and widespread use for other purposes risks inducing vancomycin-resistant *Staphylococcus* species. Metronidazole, on the other hand, is not an ideal candidate because of its ready systemic absorption, which can lead to neurotoxic side effects when given in high enough concentrations to remain effective in the gut, and the fact that it is quite bitter and thus difficult to formulate as a liquid for oral use.

Therapies to Prevent Occurrence of Pathogenic Bacterial Overgrowth and Attendant Disorders It is desirable to prevent, rather than merely treat, the gastrointestinally mediated neurological disorders discussed herein, by reducing the extent of normal bacterial disruption in the gut during antimicrobial treatment for other infections. This can be done by not using antibiotics for viral or other non-bacterial infections, but if an antibiotic must be used, it should be tailored as specifically as possible against the identified or most likely causative agent.

For example, one common drug to avoid in treating infections in young children is trimethoprim/sulfamethoxazole because it has been anecdotally indicated by parents of late onset autistic children as a common background factor (use of this antimicrobial for, e.g., ear infections, just prior to onset of autistic symptoms). This drug has also been shown to cause major overgrowth of clostridia in the bowel flora of adults (see, e.g., Haralambie et al., *Infection* 11(4): 201-4 (1983). On the other hand, in the methods of the invention, a drug such as ampicillin may have a good spectrum of activity against the pathogens of otitis media (principally *Streptococcus pneumoniae* and *Haemophilus influenzae*) and is also active against clostridia, so would not likely to lead to overgrowth of clostridia in the bowel flora. It may need to be combined with a β-lactamase inhibitor such as sulbactam.

Another embodiment of the invention that may be considered is the alternative medicine approach in which phytonutrients (plant products) such as curcumin or hops may be used with good effect and little or no toxicity.

It is important to use agents with as narrow and specific a spectrum as possible for the disorder being treated. A different or supplemental approach (discussed more fully below) is to replenish the eliminated flora as quickly as possible with probiotic or prebiotic treatment to prevent overgrowth of the problem clostridia.

Another embodiment of the invention is to immunize children in such a way that they obtain immunity at the level of the gut mucosa to the toxin involved. This involves eliciting an immunoglobulin response specific against exposed antigens of the *Clostridium* or *Desulfovibrio* toxin or toxins. Cell-mediated immunity is also important in mucosal immunity to various pathogens (van Ginkel el al., *Emerging Infect. Dis.*, 6:123-132, 2000. The pathogenic effect of overgrowth of the bacterial species involved (those producing the neurotoxins), even if it occurs, is then rendered harmless by the immune response against the toxin locally, at the gut where the toxin is produced. Eliciting this response (e.g., via B cells aggregated in the Peyer's patches/lymph nodes of the intestine) involves an antitoxin to the toxin, toxoid, or modified toxin that would induce immunity to the toxin. The data provided in the Examples below demonstrate that one or more toxins with homology to tetanus toxin (tetanospasmin) are responsible for the neurological symptoms seen in, e.g., late onset autistic children, and a region of high homology among two or more toxin genes is the preferable region or epitope to use to induce the antigenic response.

Since tetanus toxin is a member of the family of zinc endopeptidases, the use of a selective synthetic or natural zinc endopeptidase inhibitor is also a therapeutic option to reverse or prevent the neurological effects of chronic or subacute *Clostridium* infection and resultant toxin release. Examples of pseudotripeptide compounds useful in this respect, containing an ethylene sulfonamide or an m-sulfonamidophenyl moiety as the P1 side chain and natural amino acids in the P1' and P2' components, can be found in Martin et al., *J. Med. Chem.*, 42(3):515-525 (1999), herein incorporated by reference. Captopril, an oral medication well tolerated by children, is such an inhibitor and inactivates tetanus toxin in vitro.

As a last resort, surgical or pharmacologic vagotomy may be used in especially refractory cases of neurologic disorder caused by clostridial neurotoxin. The rationale is that tetanus toxin is known to travel retrogradely up the vagus nerve (which innervates the gastrointestinal tract), and vagotomy would prevent transmission of toxin from the gut to the brain, thus alleviating the neurological symptoms and preventing recurrence.

Probiotic Therapy

A preferred therapy, however, alone or in conjunction with one or more of the therapies discussed herein, is probiotic therapy. "Probiotic" therapy is intended to mean the administration of organisms and substances which help to improve the environment of the intestinal tract by inhibiting the disproportional growth of bacteria which produce toxins in the intestinal tract. For example, in healthy humans, the bowel is colonized by *Bifidobacterium*, lactobacilli (e.g., *L. acidophilus*), gram-negative anaerobes, enterococci, *Bacteroides* sp., *Parabacteroides, Prevotella, Porphyromonas*, gram-positive anaerobic cocci, *Clostridium* sp., Enterobacteriaceae (mainly *E. coli*), and enterococci and other less well-known bacteria. Some of these bacteria produce substances which suppress harmful bacteria; for example, bifidobacteria produce lactic and acetic acid, decreasing the pH of the intestines. They can also activate macrophages, which also help suppress harmful bacteria.

The best strains for supplementation are those that are typically permanent residents of the human intestinal tract and which do not produce toxins. Normal human intestinal flora are better adapted to the environment (bile acids, anaerobic conditions, etc.) of the human intestinal tract, and are more likely to survive and colonize the human intestinal tract. Certain species such as *L. bulgaricus* and *S. thermophilus*, for example, are commonly used as probiotics, but are not normal constituents of human gut flora, and such species apparently do not colonize the intestinal tract well.

The probiotic therapy of the invention is designed to be administered as a mixture of a number of species that are normal, benign inhabitants of the gut, preferably in the general proportion in which they are found in healthy humans. For example, *E. coli* is a common enteric inhabitant, but makes up only about 1/1000 of the bowel flora found in healthy humans, so would be a relatively small proportion of a probiotic mixture. Description of normal human gut flora and relative abundances can be found in Tables 1-2 below, Finegold (*J. Assoc. Anaerobic. Infect. Res.* 28:206-213 (1998), and Finegold et al. (Normal Indigenous Intestinal Flora, Chap. 1, in Hentges, D. J., ed. Human Intestinal Microflora in Health and Disease, New York, Academic Press, p. 3-31, 1983; which are incorporated herein by reference.

TABLE 1

Prevalence of major organisms in fecal flora

|  | % Stools Positive | Mean Count/gm (Log$_{10}$) |
|---|---|---|
| Gram-negative anaerobic rods | 100 | 11.3 |
| Gram-positive NSF* anaerobic rods | 99 | 11.1 |
| Anaerobic cocci | 94 | 10.7 |

TABLE 1-continued

Prevalence of major organisms in fecal flora

|  | % Stools Positive | Mean Count/gm ($Log_{10}$) |
|---|---|---|
| Clostridium | 100 | 9.8 |
| Streptococcus | 99 | 8.9 |
| Gram-negative aerobic or facultative rods | 98 | 8.7 |
| Other aerobic or facultative organisms | 93 | 6.8 |

*NSF = Nonsporeforming

TABLE 2

Most prevalent species in fecal flora

|  | % Stools Positive | Mean Count/gm ($Log_{10}$) |
|---|---|---|
| Bacteroides thetaiotaomicron | 87 | 10.7 |
| Bacteroides vulgatus | 70 | 10.6 |
| Bacteroides distasonis | 53 | 10.5 |
| Bacteroides fragilis | 46 | 10.4 |
| Bifidobacterium adolescentis group | 55 | 10.0 |
| Eubacterium aerofaciens | 49 | 9.7 |
| Clostridium ramosum | 53 | 9.1 |
| Escherichia coli | 93 | 8.6 |
| Streptococcus faecalis group | 80 | 7.5 |

A suitable probiotic mixture is composed of at least one, preferably at least three, more preferably a larger number, of the species listed in Table 2 and others in about the proportions found normally in the colon (see list in the "Mean Count/gm" column). It is estimated that, in all, there may be 300-400 species found in human colonic flora and recent research suggests 1,000 or more species.

Dosage (colony forming units (cfu) of each bacterium) is preferably at least the number found in the mean count/gram, and is supplied to the patient daily or twice daily for a number of days until it is determined that the bacteria have become established. The formulation can be provided as active cells or spores. It can be provided in an enteric coated form (e.g., for active cells) to protect sensitive cells from the gastric environment. A preferred therapy involves temporary elimination or suppression of the patient's flora (primarily or entirely with the use of antimicrobial agents) and introduction of a new, non-pathogenic flora that consists of a number of bacteria normally found in the bowel that convey colonization resistance (to prevent regrowth or re-implantation of the offending bacteria). Therapies are preferably patterned after those described in the poultry literature, for example, Wooley et al., *Avian Dis.* 43(2):245-50, (1999); Hume et al., *J. Food Prot.* 61(6):673-6 (1998); Cornier et al., *J. Food Prot.* 61(7):796-801 (1998); Hume et al., *Avian Dis.* 40(2): 391-7 (1996); Cornier et al., *Poult Sci.* 74(7):1093-101 (1995); and Cornier et al., *Poult Sci.* 74(6):916-24 (1995), all herein incorporated by reference.

Alternatively, bacteriophage specific for the bacterium producing the toxin can be introduced to the patient's gastrointestinal tract to reduce or kill the toxin-producing bacteria, and probiotic therapy mixtures can be concurrently or subsequently administered. An example of a successful protocol involving this strategy with *Clostridium difficile* can be found in Ramesh et al., *Anaerobe* 5:69-78 (1999), herein incorporated by reference. Bacteriophage may be susceptible to gastric acidity and such acidity should be neutralized prior to phage administration, or else the bacteriophage can be administered in an enterically coated tablet or capsule.

Probiotic and/or prebiotic therapy can be used in conjunction with antimicrobials used to treat infections in otherwise normal patients (i.e., before the onset of a neurological disorder) in order to prevent or reduce the risk of the occurrence of a neurological disorder. Alternatively, it can be used in conjunction with antimicrobials being used to eliminate or inhibit the abnormal microorganism(s) in a patient's gastrointestinal tract, and to promote the re-emergence of normal gut flora and proportions/balance. It is preferred that the probiotic is administered orally.

Without further description, it is believed that one of ordinary skill in the art can, using the preceding description and the following illustrative examples, make and use the present invention. The following examples are given to illustrate the present invention. It should be understood that the invention is not to be limited to the specific conditions or details described in these examples.

EXAMPLES

Example 1: Results in Autistic Children

Experiments conducted with late-onset autistic children have demonstrated success using methods of the invention. The inventors have recorded significant improvement in the symptoms of children with delayed-onset autism by providing them with antibiotics directed toward common anaerobic intestinal bacteria. By "delayed-onset," "regressive," or "late onset" autism is meant specifically an autism syndrome that appears in a child (generally between 12 and 18 months old) who has previously been developing normally. Symptoms include loss of language, social, and play skills, and onset of autistic characteristics such as avoidance of eye contact, self-stimulation behaviors, etc. Other forms of autism are clinically distinct in onset, for example early onset autism, where affected children may be born with the autistic condition or it may develop very early in life. Conventional theories are that there are genetic underpinnings to early onset autism and exposure to xenobiotics that lead to defects in normal immunity, but it is more likely in at least some cases that there is a gastrointestinal component, for example, infection with toxin-producing organisms because of a not yet fully developed normal flora (as in infant-botalism).

Eleven children with regressive onset autism were recruited for an intervention trial using a minimally absorbed oral antibiotic. Entry criteria included antecedent broad-spectrum antimicrobial exposure, followed by chronic persistent diarrhea, deterioration of previously acquired skills, and then autistic features. Short-term improvement was noted using multiple pre- and post-therapy evaluations. These included coded, paired videotapes scored by a clinical psychologist blinded to treatment status which noted improvement in 8 of 10 children studied. Unfortunately, these gains largely waned at follow-up. Although the protocol utilized is not suggested as useful therapy, these results indicate that study of a possible "gut-flora" connection warrants further investigation as it might lead to greater pathophysiologic insight and meaningful prevention and/or treatment in a subset of children with autism.

Autism is a devastating and largely untreatable disorder currently classified as a Pervasive Developmental Disorder in the DSM-IV, it usually manifests in early infancy, with impairment typically persisting into adulthood. Recent incidence estimates are one in 110 children (~10%) (CDC) with males four times more likely to be affected. Although some children are later found to have chromosomal aberrations or metabolic disorders which may explain their autistic features, no underlying etiology can be identified in the vast majority of cases. "Autistic regression" occurs in approximately one third of cases, with regression typically occurring before two years of age, and involving loss of language, social, and play skills.

Hypothesis

A number of parents of children with regressive onset autism reported to us their observation of the following sequence: repeated broad-spectrum antimicrobial use (usually for chronic otitis media), followed by chronic diarrhea, then loss of language, play, and social skills, and subsequent onset of autistic symptoms. We developed the hypothesis that repeated antimicrobial use may have disrupted a protective effect of indigenous intestinal organisms and allowed colonization by one or more neurotoxin-producing species. If this were true, then appropriately targeted antimicrobial therapy might reduce autistic symptoms in these individuals. The most plausible candidate organisms appeared to be one or more clostridial species. We now know that *Desulfovibrio* species are key organisms in autism.

Treatment Rationale

Therapeutic options include metronidazole, bacitracin, or vancomycin. The latter was chosen for its efficacy, minimal absorption (i.e., the antibiotic remains in the intestinal tract and is excreted in the stool), and benign taste (the unpleasant tasting metronidazole or bacitracin would have required a nasogastric tube for drug delivery). The decision to use vancomycin was not made lightly, however, since this drug is of paramount importance in treating life-threatening antibiotic-resistant bacterial infections, and significant public health concerns exist should its use become widespread in the community. It was used only to establish the point that autism is related to certain intestinal bacteria and that significant improvement can occur with elimination of the suspect bacteria.

Index Case

The index case was a 4.5 year old Caucasian male with chronic diarrhea and autism whose motor, cognitive, and social development was normal until 18 months of age. Diarrhea began at approximately 17 months of age after three 10 day courses of broad spectrum antimicrobials prescribed over a six week period for "chronic otitis media." There was no blood or pus in the stool nor associated constitutional symptoms. At 19 months of age there was profound behavioral and developmental deterioration, along with emergence of severe autistic features.

Extensive genetic, neurologic, gastrointestinal, and immunologic evaluations were all unrevealing. Neither conventional (e.g., full-day special education program, speech and play therapy) nor unconventional interventions (e.g., special diets, megavitamin loading) had a significant effect on his autistic symptoms.

A 12 week therapeutic trial of oral vancomycin (125 mg QID) was begun with expanded observations by a pediatric neuropsychologist pre- and post-treatment. At baseline, the child was not on a special diet nor was he taking any vitamin supplements. Three days after initiation of the vancomycin therapy, a hyperactivity pattern emerged which lasted for four days. This was followed by two days of lethargy, and subsequently by a rapid and dramatic clinical improvement. He became affectionate and relatively calm. He promptly achieved toilet training and increased vocabulary. Follow-up behavioral observations after eight weeks of therapy noted an increase in on-task performance, compliance with parental requests, awareness of environmental surroundings, and persistence when engaging in positive activities. A significant reduction in repetitive and self-stimulatory behaviors was also noted. The child's educational therapies remained unchanged for both six months before and during the vancomycin trial. Shortly after vancomycin discontinuation, behavioral deterioration was observed. Though still improved over baseline, he eventually lost most of the initial gains.

Methods

Subjects and Study Design

To explore whether our index case's improvement represented a true therapeutic effect, institutional human investigation committee approval was obtained for an open-label trial in a narrowly defined subgroup of autistic children. Eleven children (10 males, 1 female; age range: 43-84 months) were enrolled. Inclusion criteria for the study were derived from our central hypothesis and index case characteristics. They include 1) Meets diagnostic criteria for Autistic Disorder (DSM IV 299.00); 2) Other genetic and medical diagnoses have been adequately evaluated and ruled out; 3) Definable, rapid onset after 12 months of age; 4) Antecedent antimicrobial use (≤2 months of autism symptom onset); 5) Persistent loose stool history, with diarrhea onset before autism symptoms; 6) Symptoms for ≤4 years; 7) Child is 2-8 years of age; 8) No evidence of any significant medical problem that might complicate treatment such as renal, cardiac or pulmonary disease, severe enterocolitis (visible blood or pus in the stool), or chronic infection (e.g., tuberculosis); and 9) Clinically static for 3 months (no new neuroleptic, seizure, or other medications), with no elective changes during the study, and 10) No antimicrobial use for at least 2 months prior to entry into the study. All children had diarrhea and regressive onset of autistic features (occurring at a mean of 17.7±3.4 months) as previously defined in the literature.

The Developmental Profile II provided descriptive developmental levels to contrast with developmental age. While mean chronological age of the children was 59.4±12.7 months, the mean developmental age for the domains of communication (23.0 months±13.0), socialization (25.6 months±12.9), and self-help (34.4±12.4) are evidence of their significant developmental delay. The Childhood Autism Rating Scale (CARS) was also administered. The CARS is a 15-item behavioral rating scale developed to identify children with autism, and to distinguish them from developmentally handicapped children without the autism syndrome. Based upon CARS diagnostic categories, six children met the criteria for severe autism, two for moderate autism, and three for mild autism. The vancomycin dose was 500 mg/day given orally as a liquid (500 mg/6 ml), divided into 2 ml TID for eight weeks. This was followed by four weeks of oral treatment with a probiotic mixture of *Lactobacillus acidophilus*, *L. bulgaricus*, and *Bifidobacterium bifidum* ($40 \times 10^9$ cfu/ml).

Psychological Evaluations

Two measures of potential improvement were examined: I) Children were videotaped for 30 minutes at baseline and once during therapy in a playroom environment. At each session, the child was directed to play with a series of puzzles, books, blocks, and dolls by the mother and then by the evaluator. At the end of the trial, a clinical child psychologist (who was provided with a brief explanation of our working hypothesis) compared coded, paired videotapes of 10 of the 11 children studied (video was not available for one child). The psychologist viewed each pair of tapes and scored them. To diminish the possibility of investigator bias, the tapes were randomly numbered and the psychologist did not have any personal contact with the children. 2) Behavior and communication analog rating scales were completed by the study physician at baseline, during therapy, and at follow-up in a manner similar to previously validated methods for other disease states. Results are presented as median scores to account for potential non-linear score increment.

Laboratory Evaluations

Extensive medical evaluations were conducted in parallel with the detailed psychological assessments. Stools were examined for occult blood, inflammatory cells, *Aeromonas hydrophila, Cryptosporidium, Clostridium difficile* toxin, routine bacterial pathogens, and ova and parasites. Blood tests included complete blood cell counts, chemistry panels, and erythrocyte sedimentation rates. Urinalyses were also obtained. Detailed quantitative aerobic and anaerobic fecal microbiologic studies were conducted at the Wadsworth Anaerobic Bacteriology Laboratory on specimens from four children. Each stool was cultured with a total of 27 different media and atmospheric conditions, modified from the procedure described in Summanen et al.

Results

Analog Rating Scales, Videotapes, Treatment Observations and Laboratory Evaluations Unblinded assessment using an analog rating scale noted improvement for the group as a whole in communication (Wilcoxon Signed Ranks Z=2.9 p=0.003) and behavior (Wilcoxon Signed Ranks Z=−2.9, p=0.003). To insure that changes attributed to intervention were not a reflection of differences at baseline, Spearman correlations were conducted. There were no significant correlations between the baseline measure and post-intervention score for either communication (rho=0.35, p=0.28) or behavior (rho=0.22, p=0.51). Blinded assessment of the coded, paired videotapes noted an improvement during therapy in eight of ten children studied, no change in one, and a possible deterioration in one.

As previously observed in the index case, a brief (1-4 days) period of hyperactivity was noted in six children within three days of initiating antibiotic treatment. One subject then experienced a day of marked lethargy. Otherwise, aside from obvious autistic features, all children had normal physical examinations at baseline and throughout the study, as well as unremarkable basic blood, stool, and urine tests as outlined in the Methods section.

Long-Term Follow-Up

Although apparent improvement was clear by several measures, unfortunately these gains did not endure. One child who had responded significantly to treatment, deteriorated towards the end of the study while still on vancomycin therapy. During telephone follow-up (conducted weekly during the probiotic therapy), most parents reported substantial behavioral deterioration within two weeks of discontinuance of vancomycin treatment. Due to difficulty in disguising the taste, probiotic treatment compliance was very poor in several children. Behavioral deterioration appeared to occur whether or not the child was compliant with the probiotic therapy regimen. Therefore, it would appear that the probiotic therapy used as an adjunct after vancomycin treatment had no discernible beneficial or adverse effect. All children were observed in follow-up, ranging from two to eight months after discontinuance of vancomycin. In all but one child, the analog ratings returned towards baseline.

Quantitative Fecal Flora

Given the extreme labor intensiveness of such studies, it will be some time before detailed microbiologic analysis of all pre- and post-therapy stool specimens is completed. Stool specimen data from four autistic children prior to vancomycin therapy were compared to those of 104 normal adult subjects from previously published studies (performed under the supervision of the same principal investigator). Anaerobic cocci, chiefly peptostreptococcal species, were present in 93% of the adults' specimens, comprising some 10% of the stool microorganisms. In stark distinction, these species were absent from the stools of each of the four autistic children tested (Table 3).

TABLE 3

Fecal Flora Data

| Organism | Autistic Patient A | Autistic Patient B | Autistic Patient C | Autistic Patient D | Adults (104 Subjects*) |
|---|---|---|---|---|---|
| Enterobacteriaceae | 6 | 7 | 7 | 7 | 9 |
| *Streptococcus* | 3 | 5 | 0 | 4 | 9 |
| *Enterococcus* | 0 | 6 | 0 | 0 | 8 |
| *Bacteroides fragilis* grp | 8 | 8 | 9 | 8 | 11 |
| *Bacteroides*, other | 8 | 0 | 9 | 8 | 11 |
| Anaerobic GNR, other | 6 | 4 | 7 | 5 | 8 |
| *Peptostreptococcus* spp. | 0 | 0 | 0 | 0 | 10** |
| Anaerobic cocci, other | 0*** | 0 | 0**** | 0 | 11** |
| *Lactobacillus* spp. | 9 | 9 | 10 | 8 | 10 |
| *Bifidobacterium* spp. | 7 | 9 | 9 | 8 | 10 |
| *Eubacterium* spp. | 8 | 0 | 9 | 8 | 11 |
| *Clostridium* spp. | 9 | 7 | 8 | 8 | 10 |

Units are $\log_{10}$ colony forming units (cfu) gram dry weight.
*Mean of positive specimens. Subjects were normal adults on various diets (vegetarian, traditional Japanese diet, or standard Western diet); there were no statistically significant differences in the results between these various groups.
**93% of the 104 subjects had *Peptostreptococcus* spp. and/or other anaerobic cocci.
***Ethanol and heat-resistant coccoid forms were present (probably clostridia.)
****Heat-resistant coccoid forms were present (probably clostridia.)

Discussion

The apparent, though short-term, improvement during treatment with this minimally absorbed antibiotic is not explainable using current conventional genetic hypotheses' alone for autism. Results of this preliminary study, along with previous reports of increased intestinal permeability and a "nonspecific colitis" in children with autism, suggests a possible "gut-brain" etiologic connection may be present in a subset of these children.

Although the hypothesis that autism (in a defined subset of children) may be a sequela to the colonization of the intestinal tract by one or more neurotoxin-producing bacteria is novel, published data along several paths may lend credence to the notion that an alteration in colonic flora contributes to autism symptoms. The first line of evidence is from the infant botulism literature. This condition was first recognized as a distinct clinical entity in 1976. It differs from classical (foodborne) botulism in that the intestinal tract becomes colonized by *Clostridium botulinum* and elaboration of the neurotoxin occurs in vivo. Age is a primary risk factor for the development of infant botulism as diagnosis of the disease is rare after 1 year of age. Studies in animals have demonstrated a similar age-dependent susceptibility. However, the colonization resistance observed in mature animals is greatly diminished when they are treated with broad-spectrum antimicrobials. Similarly, antimicrobial use has been identified as a risk factor for the development of botulism related to intestinal colonization with *C. botulinum* in older children and adults.

The second line of evidence is from human and animal studies which have repeatedly demonstrated that intestinal colonization by opportunistic pathogens (e.g., *Escherichia coli, Klebsiella pneumoniae, Pseudomonas aerguinosa, Salmonella enteritidis, Shigella flexneri*, and *Vibrio cholerae*) is greatly enhanced when protective intestinal microbiota is disrupted by broad-spectrum antimicrobials. In humans, the best-documented example of opportunistic colonization of the intestinal tract following antimicrobial use is that by *Clostridium difficile*, the causative agent of pseudomembranous colitis.

Another potentially relevant condition is d-lactic acidosis, in which associated psychiatric symptoms are well-documented. D-lactic acidosis, a complication of short bowel syndrome or intestinal bypass surgery for obesity, is a condition caused by a change in bacterial flora to an acid-tolerant, aciduric (*Lactobacillus, Bifidobacterium, Eubacterium*, and *Streptococcus*) flora. Patients present with a range of behavioral changes such as hostility, slurred speech, stupor, altered mental status, dizziness, asterixis, and ataxia. Treatment is with appropriate oral antimicrobials, resulting in rapid cessation of neurological signs.

For quantitative measurement of improvement in autistic symptomatology, the current study utilized two independent assessment tools. Although the analog rating scales were completed by the study physician who was aware of the children's treatment status, the formal videotape ratings were performed in a blinded manner. The improvement observed after vancomycin intervention appeared to be significantly greater than could normally be attributable to the characteristic waxing and waning of autistic symptomatology.

A substantial deterioration of the behavioral improvements made while on therapy was reported by most parents within two weeks of ending the vancomycin trial. While the cause for neither the apparent improvement nor the later decline is known, it is possible the deterioration is due to the offending organism being spore-forming, and hence surviving therapy to germinate after vancomycin discontinuation, as has been documented with *Clostridium difficile* infection. An additional possibility is that the therapy was sublethal due to antimicrobial choice and/or dosage regimen permitting emergence of antimicrobial-resistant bacteria.

Since vancomycin is not absorbed, it appears likely that the behavioral improvement was related, in some way, to the drug's effect on the intestinal tract flora (and not a "drug effect" per se on the central nervous system). Although we theorize that the transient benefit from vancomycin treatment may be due to the temporary elimination of a neurotoxin-producing pathogen, there are other possible mechanisms. For example, autoantibodies to neuron-axon filament protein, glial fibrillary acidic protein, and myelin basic protein have been reported in autism and it has been postulated that these autoantibodies may contribute to autistic symptomotology. It is at least theoretically possible that the production of these autoantibodies is related to the presence of an infectious pathogen as has been postulated for rheumatoid arthritis.

The significance of the possible fecal flora changes in these autistic children is unknown. It is unlikely that specimen collection or shipping contributed to the absence of *Peptostreptococcus* and other anaerobic cocci as other equally oxygen-sensitive organisms were recovered. Although all of the children had previously received broad-spectrum antimicrobials (capable of severely disrupting intestinal flora), fecal bacterial counts typically return to their pre-treatment composition within two weeks of discontinuance of the antimicrobial agent.[iv] Therefore, since none of the children, at base line, had a history of antimicrobial treatment for at least two months prior to entering our study, it is unlikely that the absence of these species reflects a transient alteration in the children's fecal flora. An uncharacterized *Peptostreptococcus* species has been documented to inhibit certain organisms, including clostridia, in vitro and in animals, and it is intriguing to speculate that the absence of such organisms in certain autistic children may permit growth of clostridial or other toxin-producing bacteria through loss of competitive inhibition.

The fecal flora of pediatric subjects has been extensively studied. Use of normal adult control fecal specimens in the present study, though not ideal, is justifiable given documented similarity to pediatric stool flora. For example, one recent review of bacterial colonization patterns states that "by 12 months (of age) the anaerobic fecal populations begin to resemble that of adults in number and composition as the facultative anaerobes decrease. By two years of age, the profile resembles that of the adult."

Example 2: Culture Conditions, Antimicrobial Susceptibility Determination

Culture Conditions

We use a selective medium for clostridia that contains (per liter) 25.0 g of brain heart infusion (BBL, USA), 20.0 g of agar (Sigma, USA), 76.0 mg of sulfamethoxazole, 4.0 mg of trimethoprim, 1.0 mg of vitamin K, 5.0 mg of heroin, and 50.0 ml of laked sheep blood. All medium components except the two antimicrobial agents and the laked sheep blood are mixed, autoclaved at 121° C. for 15 mins and cooled to 50° C. in a water bath, at which point the three initially omitted ingredients are added. An additional medium is made up in identical fashion except that 30.0 to 50.0 g of agar is used, rather than 20.0, in order to make the medium stiffer and thus minimize spreading of clostridial colonies.

Stock solutions of antimicrobials are prepared separately in advance by aseptically dissolving the sulfamethoxazole in half volume hot water with a minimal amount of 2.5 M NaOH and the trimethoprim in 0.05 N lactic acid or HCl, 10% of final volume. The stock solutions are stored at −20°

C. before addition to the selective medium. After the medium is poured into Petri dishes, the plates are dried and placed into an anaerobic chamber and reduced for approximately 24 hours. They are then stored in the chamber at ambient temperature (25° C.) for at least two days, but no longer than seven days, before use.

The entire stool specimen is weighed before processing. It is then placed into an anaerobic chamber and homogenized in a heavy duty blender with no diluent (if liquid) or with one or two volumes of diluent (0.05% yeast extract) added if the stool is soft or fully formed. Homogenization is carried out because we have found previously that organisms are not distributed evenly throughout the fecal mass; this avoids sampling errors. Serial ten-fold dilutions of the specimen are then made in 9 ml dilution blanks (Anaerobe Systems, USA) and 100 µl of each dilution from $10^{-1}$ through $10^{-8}$ is inoculated onto the selective medium (both agar concentrations) and onto a Brucella blood agar plate. The fecal suspensions ($10^{-1}$-$10^{-5}$) are also heated at 80° C. for 10 minutes (to select out clostridial spores) and 100 µl of each dilution is inoculated onto the selective media and the Brucella blood agar.

After 5 days of incubation of the inoculated plates at 37° C., each colony type from both heat-treated and non-treated specimens is counted from a dilution plate containing between 30 and 300 colonies of the type being isolated. Total bacterial counts, in addition to clostridial counts, are also recorded from the Brucella blood agar plates.

In order to correct for differing moisture content in different specimens of stool, a portion of sample (~1 g) is placed onto a pre-weighed drying dish. The dish is again weighed and then placed into a drying oven and incubated at 70° C. (with 18-20 inch Hg vacuum) for 48 hours. After this incubation, the dish with the specimen is re-weighed so that bacterial counts can be corrected for moisture content.

Identification of Isolated Bacteria

The identification of isolated colonies as clostridia, and speciation of these, is done by methods outlined in the Wadsworth Anaerobic Bacteriology Manual, 5th Edition (Summanen et al., Star Publ. Co., Belmont, Calif., 1993, herein incorporated by reference) including, when indicated, cellular fatty acid analysis in a MIDI capillary column gas chromatograph, 16S rDNA sequencing, and DNA-DNA hybridization (the latter two procedures as outlined in a paper from this laboratory (Wexler H M et al., *Int. J Syst Bacteriol* 46:252-258, 1996, herein incorporated by reference).

Antimicrobial Susceptibility Determination

Testing of susceptibility of isolated clostridia to antimicrobial agents such as vancomycin, metronidazole, bacitracin and ramoplanin is done by two different techniques—the NCCLS Wadsworth agar dilution procedure (Methods for Antimicrobial Susceptibility Testing of Anaerobic Bacteria, Approved Standard-Fourth Edition. NCCLS Publication M 11-A4, Wayne, Pa.: NCCLS, 1997, Vol. 17, No. 22, all herein incorporated by reference) and the spiral gradient endpoint procedure (Wexler H M et al., *J Clin Microbiol* 34:170-174, 1996, herein incorporated by reference).

Example 3: Testing for Toxin Polypeptides

ELISA Testing—Rationale and Methods

Since all of the known clostridial neurotoxins share significant amino acid homology, low-level cross-reactivity of antibodies has been reported. This will allow us to detect a clostridial neurotoxin that is closely related to, but not identical with, tetanus toxin.

Media containing hydrolysates of casein improve the production of all known clostridial neurotoxins. Therefore, the cells were grown in Brain Heart Infusion Broth (Becton Dickinson, 20 Sparks, Md.) supplemented with 2.5% pancreatic digest of casein (Tryptone Peptone, Becton Dickinson). After five days of growth, the culture supernatants were clarified by centrifugation at 4000×g and filter-sterilized through a 0.45 µl nitrocellulose membrane filter. Antigens from known *C. tetani* strains (ATCC 10779, 19406, 453, 9441) and tetanus toxoid (Lederle, Pearl River, N.Y.) were used for initial optimization experiments and subsequently as positive controls.

Our methods are based upon previously standardized ELISA protocols for direct competitive detection of soluble antigens (Current Protocols in Molecular Microbiology). The wells of solid-phase immunoassay microtiter plates (Biotech Diagnostic, Niguel, Calif.) are inoculated with 50 µl of antigen solution, sealed with plastic wrap and incubated overnight at room temperature. The plates are washed three times with deionized water to remove unbound antigen solution. The wells are then filled with a blocking buffer (Tween 20 0.05% and bovine serum albumin 0.25%) and incubated at room temperature for 30 minutes. The plates are again washed three times prior to addition of 50 µl of serially diluted antibody solution; 1:1000 to 1:10,000 dilutions of polyclonal IgG goat tetanus exotoxin (Fitzgerald, Concord, Mass.). Plates are sealed with plastic wrap and incubated at room temperature for two ⊇ hours. After washing, rabbit anti-goat IgG alkaline phosphatase conjugated antibodies (Fitzgerald) are added and the plates incubated at room temperature overnight. A microtiter plate reader was used to measure the fluorescence.

ELISA Results

All four ATCC strains of *C. tetani* consistently produced positive results. This is interesting to note because *C. tetani* strain ATCC 19406 does not consistently yield positive PCR results. One possible explanation may be that ATCC 19406 produces a toxin immunologically similar (or identical) to other *C. tetani* strains but its genetic code for toxin production is slightly different During initial testing, we noticed that all *C. perfringens* strains (ATCC type strain, strains from children with autism, and strains from normal children) yielded positive results. This might be due to cross-reactivity of the antibodies against tetanolysin (a hemolysin produced by *C. tetani* strains) with perfringolysin—a very closely related hemolysin. We performed Western blot testing so that the size of the immunoreactive proteins could be visualized and compared to positive controls.

Western Blot Testing

The cells were grown in Brain-Heart-Infusion Broth (Becton Dickinson, Sparks, Md.) supplemented with 2.5% pancreatic digest of casein (Tryptone Peptone, Becton Dickinson). After four days of incubation at 37° C. and an additional two days at 4° C. (to enhance sporulation, lysis and release of toxin), the culture supernatants are clarified by centrifugation at 4000×g and filter-sterilized through a 0.45 µm nitrocellulose membrane filter. *Clostridium tetani* strains (ATCC 10779, 19406, 453, 9441) and tetanus toxoid (Lederle, Pearl River, N.Y.) were used for initial optimization experiments.

Our methods are based upon previously standardized protocols for immunoblotting and immunodetection (Western blotting) of soluble antigens (Current Protocols in Molecular Microbiology, vol. 2, 1997, pp. 10.8.1-21). Briefly, the filtered culture supernatant is solubilized with a detergent (SDS) and a reducing agent is included to reduce sulfhydryl bonds. The solubilized proteins are separated by SDS-polyacrylamide gel electrophoresis (SDS-PAGE). The gel is then electroblotted resulting in transfer of the protein bands to a nitrocellulose membrane. The membrane is placed in a tray with blocking buffer, 2% skim milk in phosphate-buffered saline (PBS), and kept at room temperature for 1 hour. Primary antibody, polyclonal IgG goat tetanus antitoxin (Fitzgerald, Concord, Mass.), diluted 1:1,000 in blocking buffer is then added. Following a 1-hour incubation, the membrane is washed four times with PBS. The detection of antibody binding occurs with rabbit anti-goat-IgG conjugated to alkaline phosphatase. When substrate is added, a colorimetric reaction occurs, thus indicating that the initial (anti-tetanus serum) antibody was bound by a protein on the membrane. (Sigma, St. Louis, Mo.) Anti-Ig conjugate, 1:1,000 dilution in blocking buffer, is added and incubated at room temperature for 1 hour. After four fifteen-minute washes, the membrane is incubated with color development buffer (100 mg/ml 4-nitro blue tetrazolium chloride (final: 0.33 mg/ml) (NBT) and 50/mg/ml 5-bromo-4-chloro-3-indolyl-phosphate (final: 0.165 mg/ml) (BCIP) added to substrate buffer: 0.05M $Na_2CO_3$, 0.5 mM $MgCl_2$ pH 10.2). The reaction is stopped by washing the membrane in distilled water for 10 minutes.

Western Blot Results

We initially tested multiple *C. perfringens* strains; the ATCC type strain, a strain isolated from the stool of a child with autism, and a strain isolated from the stool of a normal child. All strains of *C. perfringens* produced an immunoreactive protein of the same molecular weight, which explains the positive results observed during ELISA testing. We theorize that this protein may be perfringolysin (which would be expected to cross react with anti-tetanolysin antibodies). There were, however, striking differences between these three *C. perfringens* strains. The strain from the autistic child produced additional immunoreactive proteins. Furthermore, these immunoreactive proteins appeared to be of the same molecular weight as the tetanus neurotoxin proteins (light and heavy chain, about 100 kD) produced by our *C. tetani* control strain. Repeat testing confirmed our initial results. Additional studies were performed on several clostridial species isolated from a second child with autism. One of the strains from this child, *C. beijerinckii*, produced a strongly immunoreactive protein of ~50 kDa, which is the approximate weight of the light-chain of tetanus toxin and other known clostridial neurotox ins. Western blot testing of the ATCC *C. beijerinckii* type strain will be performed. However, ELISA testing of the type strain was negative, suggesting that typical *C. beijerinckii* strains do not produce a protein that is immunoreactive with anti-tetanus antibodies.

Our colleague, has tested the filtrate of an ATCC strain of *C. tetani* in the hind leg of mice and has produced paralysis of that limb and subsequently death. We will test blinded cultures from autistic and control children for this in vivo test.

Example 4: Fecal Microflora of Autistic Children

Materials and Methods

Subjects.

33 autistic subjects, 7 non-autistic siblings and 8 control subjects considered here were enrolled in the study at the Evergreen Center in Oregon City, Oreg. and the Center for Autism and Related Disorders (CARD) in Tarzana, Calif. with signed, informed consent of their parents or guardians and approval of VA Greater Los Angeles Healthcare System Institutional Review Board IRB B. All autistic children participating in this study had an educational or developmental pediatrician evaluation and were diagnosed with autistic spectrum disorder. Subsequently, JAG evaluated each patient for autism and validated the diagnosis based on impairment in social skills, impairment in language skills and verbal communication, sensory disturbances, repetitive stereotypical behaviors, and gastrointestinal disturbances. JAG's practice has been limited to autistic spectrum disorders since 1999 and he has evaluated and treated approximately 2000 patients in that time. All autistic and control subjects were between 2 and 13 years of age. Among the autistic group, there were 24 males and nine females. Among the control group, there were five males and three females. The sibling control group consisted of five females, and two males. Based upon clinical evaluation we were able to distinguish the severity of autism in 30 of the 33 autistic subjects. Eleven subjects were categorized as severe, while 19 subjects were grouped into the mildly autistic category.

Stool Collection and Transport.

Specimens (the entire fecal specimen) were collected at the homes of the participants and were shipped to the Wadsworth Anaerobe Laboratory in Los Angeles the same day, by air express, packed with frozen blue shipping packets. The specimens always arrived in Los Angeles the next morning. In the laboratory, the specimens were thawed, homogenized in a Waring blender, and DNA was extracted. The DNA specimens were then kept frozen at −80° C. for possible further studies.

DNA Extraction.

One ml aliquots of stool, previously diluted 1:3 in sterile bi-distilled water and thoroughly homogenized under anaerobic conditions in an anaerobic chamber) were centrifuged at 14,000×g for 3 min to pellet fecal bacterial cells. The supernatant was carefully removed and discarded. Two hundred milligrams of cell pellet was transferred to a fresh tube and subjected to DNA extraction using a commercial extraction system (QIAamp DNA stool mini kit; Qiagen) according to the instructions of the manufacturer. Previous studies in our laboratory have shown that the QIAamp product produces high-quality DNA free of PCR-inhibiting substances. DNA extraction was performed in duplicate.

Blinding of Information.

Information on which specimens came from autistic children and which from control children was withheld from the investigators doing the pyrosequencing until their data set was completed. Subsequently, this information was provided to them by the group in Oregon so that proper group analyses of the data could be completed.

bTEFAP.

bTEFAP was utilized with titanium chemistry, as described previously by the Dowd laboratory (Dowd et al. *PLoS ONE* 3, e3326, 2008; Dowd et al. *Foodborne Pathog. Dis.* 5, 459-472, 2008; and Dowd et al. *BMC Microbiol.* 8, 125, 2008; which are incorporated herein by reference), to evaluate the bacterial populations in the feces of separate autistic children in comparison to individual control samples. In preparation for FLX sequencing (Roche, Nutley, N.J.), the DNA fragments' size and concentration were accurately measured. A small sample of double-stranded DNA molecules/μl was combined with DNA capture beads, and then amplified by emulsion PCR. After bead recovery and bead enrichment, the bead-attached DNAs were denatured with NaOH, and sequencing primers were annealed. A 454 sequencing run was performed using the Genome Sequencer FLX Titanium System (Roche, Nutley, N.J.). All FLX-Titanium procedures were performed using Genome Sequencer FLX System manufacturer's instructions (Roche, Nutley, N.J.).

bTEFAP Sequence Processing Pipeline.

Custom software written in C# within a Microsoft® .NET (Microsoft Corp, Seattle, Wash.) development environment was used for all post-sequencing processing. Quality trimmed sequences obtained from the FLX Titanium sequencing run were derived directly from FLX Titanium sequencing run output files. Tags were extracted from the multi-FASTA file into individual sample-specific files based upon the tag sequence. Sequences which were less than 350 base pairs after quality trimming were not considered. Sequences were analyzed by a script optimized for high throughput data. Definite chimeras were removed using B2C2 (software are available at http://researchandtesting.com/B2C2). The resulting FASTA for each sample, with chimeras removed, were then evaluated using BLASTn against a custom database derived from NCBI, curated based upon quality criteria similar to that utilized for high quality sequences of the RDP-II database. C# scripts were used to extract necessary taxonomic information from NCBI for the accession numbers derived from the database queries.

Microbial diversity analysis was performed by clustering sequence tags into groups of defined sequence variation ranging from unique sequences (no variation) to 10% divergence evaluated, as previously described, from raw reads of comparable Phred20 quality (>350 bp) (Acosta-Martines et al., *Soil. Biol. Biochem.* 40:2762-2770, 2008, which is incorporated herein by reference). Clusters acting as OTUs were used to generate rarefaction curves and as input for calculations with the abundance-based coverage estimator ACE and the Chao1 (Chao et al., *Biometrics* 58, 531-539, 2002, which is incorporated herein by reference) estimator of species diversity. Table 7 shows the microbial diversity estimate averages and t-test results obtained with (parametric and non-parametric) modeling of rarefaction, ACE and Chao1. Final datasets classified at the species and other relevant taxonomy levels were compiled into separate worksheets. To assess not only the overall bacterial richness of the samples, but the actual populations, we conducted a "composition analysis". This process produced results containing information for each sample at each taxonomic level (kingdom, phylum, class . . . ).

Statistics.

Principal Component Analysis

To assess the separability of the samples, Principal Component Analysis was implemented. Principal Component Analysis (PCA) (HSPH. Autism Has High Costs to U.S. Society. Harvard School of Public Health. (2006) http://www.hsph.harvard.edu/news/press-releases/2006-releases/press04252006.html) is widely used for dimensionality reduction to help with visualization of high dimensional data. PCA is defined as the orthogonal projection of the data onto two or three dimensional space such that the variance of the projected data is maximized. Custom Python scripts tailored for next generation data (distance matrices and taxonomic abundance) were implemented to assess bacterial composition of samples and determine the 3 Principal Components. This data is visualized by plotting the samples on axes defined by the principal components. Samples more similar to each other should appear closer together according to the respective axis reflecting the variation among all samples. This technique is useful in displaying clusters existing within data. The variables (features) are the relative bacterial composition in a sample at a particular taxonomic level.

Clustering

To analyze the relationships and clustering between autistic and control samples, double dendrograms were formed based on the bacteria composition information. The analysis was performed using the NCSS Statistical Software as described previously (Acosta-Martines et al. 4 *Soil. Biol. Biochem* 40, 2762-2770, 2008; Bailey et al. *Biol. Lett.* ePub ahead of print, 2010; Dowd et al. *Foodborne. Pathog. Dis.* 5, 459-472, 2008; Suchodolski et al. *BMC Microbiol.* 9, 210, 2009; and Wolcott et al. *BMC Microbiol.* 9, 226, 2009; which are incorporated herein by reference).

Other Statistics

As appropriate, student's t-tests were used for comparing means within various groups of data.

Results and Discussion

The results indicate there is a significantly higher diversity of bacteria found in the feces of autistic subjects compared to controls (Table 4).

TABLE 4

Diversity and richness data for groups of subjects in the study. Data are presented at the 1% divergence level (corresponding roughly to the strain of bacteria), the 3% divergence level (corresponding roughly to the species level) and the 5% divergence level (corresponding roughly to the genus level) for rarefaction maximum predicted (RFM), ACE, and Chao1 estimates. The P-values (p-val) corresponding to a T-test evaluation, indicate that the controls have significantly lower numbers of operational taxonomic units than the autistic subjects.

|  | RFM 1 | RFM 3 | RFM 5 | ACE 1 | ACE 3 | ACE 5 | Chao1 1 | Chao1 3 | Chao1 5 |
|---|---|---|---|---|---|---|---|---|---|
| Group Means |  |  |  |  |  |  |  |  |  |
| Mild Autism Mean | 886 | 558 | 376 | 2627 | 1181 | 584 | 2265 | 1055 | 562 |
| Mild Autism St. Dev | 417 | 284 | 192 | 1519 | 680 | 326 | 1298 | 607 | 329 |
| Severe Autism Mean | 914 | 564 | 375 | 2402 | 1122 | 567 | 2135 | 1052 | 546 |
| Severe Autism St. Dev | 240 | 150 | 107 | 665 | 330 | 192 | 583 | 297 | 186 |
| All Autism Mean | 871 | 542 | 364 | 2455 | 1118 | 561 | 2142 | 1018 | 541 |

TABLE 4-continued

Diversity and richness data for groups of subjects in the study. Data are presented at the 1% divergence level (corresponding roughly to the strain of bacteria), the 3% divergence level (corresponding roughly to the species level) and the 5% divergence level (corresponding roughly to the genus level) for rarefaction maximum predicted (RFM), ACE, and Chao1 estimates. The P-values (p-val) corresponding to a T-test evaluation, indicate that the controls have significantly lower numbers of operational taxonomic units than the autistic subjects.

|  | RFM 1 | RFM 3 | RFM 5 | ACE 1 | ACE 3 | ACE 5 | Chao1 1 | Chao1 3 | Chao1 5 |
|---|---|---|---|---|---|---|---|---|---|
| All Autism St. Dev | 352 | 238 | 161 | 1250 | 565 | 274 | 1065 | 503 | 273 |
| Control Mean | 491 | 296 | 209 | 1234 | 567 | 308 | 1092 | 530 | 300 |
| Control St. Dev | 64 | 66 | 39 | 462 | 209 | 78 | 318 | 167 | 70 |
| Sib Control Mean | 1120 | 704 | 473 | 3032 | 1435 | 740 | 2694 | 1331 | 732 |
| Sib Control St. Dev | 319 | 237 | 155 | 1079 | 529 | 256 | 883 | 461 | 259 |
| Group Student's T-test p values |  |  |  |  |  |  |  |  |  |
| Severe vs control | 0.000 | 0.000 | 0.000 | 0.000 | 0.000 | 0.001 | 0.000 | 0.000 | 0.001 |
| control vs all aut | 0.002 | 0.003 | 0.005 | 0.005 | 0.005 | 0.007 | 0.005 | 0.005 | 0.009 |
| control vs sib control | 0.000 | 0.000 | 0.000 | 0.000 | 0.000 | 0.000 | 0.000 | 0.000 | 0.000 |
| sib vs severe aut | 0.068 | 0.071 | 0.064 | 0.071 | 0.070 | 0.060 | 0.062 | 0.067 | 0.047 |

Even when relatively large genetic distances (5% divergence) are considered, these estimates predict that even at the genus level there is significantly less diversity (at a 5% significance level) and richness of microbial communities in control subjects than in the autistic group. These diversity results were similar when using three separate diversity and richness methods (including Chao 1, ace, and rarefaction). From this data we see that the parametric method of rarefaction (Acosta-Martines 2008) predicts that the average number of operational taxonomic units present in the feces of all autistic samples at 3% sequence divergence (the species level) was 542 compared to 296 in the control samples. Using the ace non-parametric measure of richness, we see that there are a predicted 1118 species in the autistic samples and 567 in the control samples and based upon Chao1 there were an average of 1018 and 530, respectively. This dramatic and significantly increased diversity and richness may be an important aspect of the autistic gastrointestinal microbiome. The increased microflora of autistic children may contain harmful genera or species contributing to the severity of autistic symptoms. Decreasing harmful populations with antibiotics like vancomycin has been shown to be an important step in improving late onset autism symptoms.

The OTU data also indicates no statistically significant difference between the sibling control subjects and the severely autistic subjects. However, when comparing the true controls against sibling controls, the estimated richness does prove to be statistically different. This and other tests discussed later indicate the sibling controls to be more similar to autistic children than to the true control subjects.

Summary information at the phylum level for all four groups of samples (severely autistic, mildly autistic, control and sibling control) are shown in Table 5.

TABLE 5

Bacterial composition at the phylum level for control, sibling control, mildly autistic and extremely autistic subjects (3 autistic children were not considered because of unknown severity). The phylum designation is shown under the "Phylum" column. The next four columns display the percentage at which the specified phylum can be found in a specific sample with a standard deviation proceeded with a "+/−". Non-existing standard deviations are designated with a 0.0. Control samples are designated under "Control", sibling controls are in the "S-Control" column, levels for mildly autistic subjects are under "Mild-Autism", while samples from the severely autistic are in the "Severe-Autism" column. Phyla not found in a group of samples are designated with a 0.0. The t-test based p-value is listed in the p-value column.

| Phylum | Control (n = 8) | S-Control (n = 7) | Mild-Autism (n = 19) | Severe-Autism (n = 11) | p-value Severe-Aut vs. Control |
|---|---|---|---|---|---|
| Firmicutes | 63.631 +/− 17.593 | 44.012 +/− 24.576 | 38.975 +/− 15.434 | 38.015 +/− 13.772 | 0.001 |
| Actinobacteria | 1.812 +/− 1.679 | 1.037 +/− 1.515 | 0.732 +/− 1.426 | 0.464 +/− 0.597 | 0.012 |
| Bacteroidetes | 30.226 +/16.413 | 44.326 +/− 17.794 | 51.591 +/− 12.237 | 51.248 +/− 7.043 | 0.001 |
| Proteobacteria | 0.535 +/− 0.428 | 2.327 +/− 3.789 | 2.281 +/− 2.414 | 3.122 +/− 2.579 | 0.011 |

TABLE 5-continued

Bacterial composition at the phylum level for control, sibling control, mildly autistic and extremely autistic subjects (3 autistic children were not considered because of unknown severity). The phylum designation is shown under the "Phylum" column. The next four columns display the percentage at which the specified phylum can be found in a specific sample with a standard deviation proceeded with a "+/−". Non-existing standard deviations are designated with a 0.0. Control samples are designated under "Control", sibling controls are in the "S-Control" column, levels for mildly autistic subjects are under "Mild-Autism", while samples from the severely autistic are in the "Severe-Autism" column. Phyla not found in a group of samples are designated with a 0.0. The t-test based p-value is listed in the p-value column.

| Phylum | Control (n = 8) | S-Control (n = 7) | Mild-Autism (n = 19) | Severe-Autism (n = 11) | p-value Severe-Aut vs. Control |
|---|---|---|---|---|---|
| Verrucomicrobia | 5.031 +/− 7.920 | 9.498 +/− 13.214 | 8.092 +/− 7.968 | 8.079 +/− 11.990 | 0.227 |
| Cyanobacteria | 0.318 +/− 0.178 | 0.256 +/− 0.408 | 0.090 +/− 0.117 | 0.069 +/− 0.075 | 0.099 |
| Fusobacteria | 0.081 +/− 0.0 | 0.0 | 0.024 +/− 0.010 | 0.024 +/− 0.0 | 0.194 |
| Tenericutes | 0.0 | 0.110 +/− 0.079 | 0.789 +/− 0.117 | 0.167 +/− 0.209 | 0.098 |
| Lentisphaerae | 0.0 | 0.0 | 0.037 +/− 0.0 | 0.0 | 0.0 |

Figure 1B:
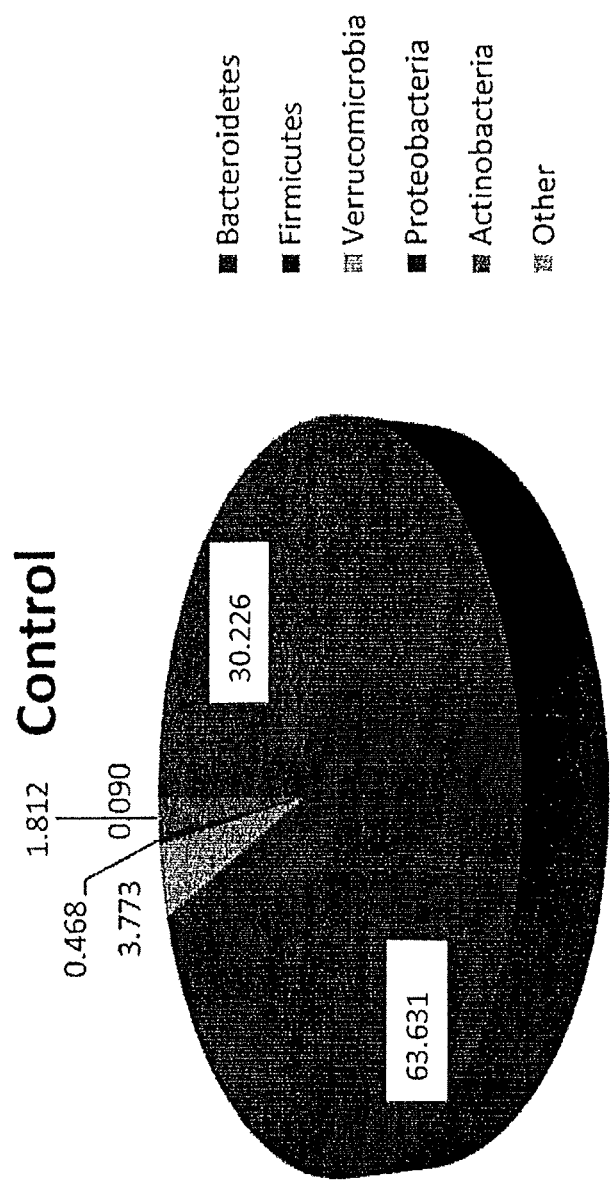
Figure 1C:
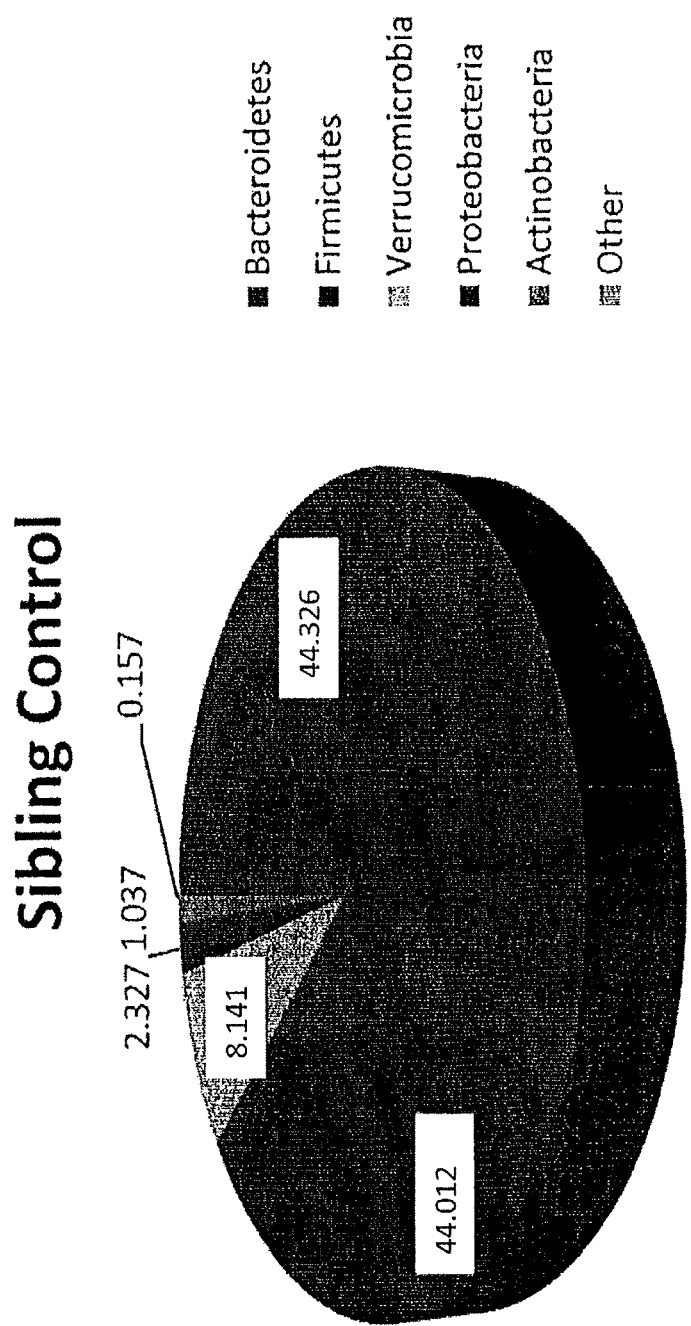

Bacteroidetes and Firmicutes are shown to be important phyla in this analysis. There are also significant differences between severely autistic subjects and controls with regard to the Actinobacterium and Proteobacterium phyla. A trend can be seen in Firmicutes where the level of this phylum is much higher in the control than autistic samples. Taxonomically, it is not surprising at the phylum level that Bacteroidetes (Table 5) were significantly higher in counts in autistic subjects (p 0.001) while Firmicutes tended to be higher in the control subjects (p 0.001). These data provide points to an altered microflora in the gut of autistic subjects. FIGS. 1A-1C show the composition of autistic and control and sibling control samples, respectively, and again emphasize the difference between the autistic and control groups. The sibling control figure (FIG. 1C), proportionally looks to be between the autistic and control groups, as might be expected. However, similar to the autistic group, Firmicutes comprises less than 50% of the bacteria, unlike in the control group where Firmicutes represents an average of 63.6%.

Figure 2A:
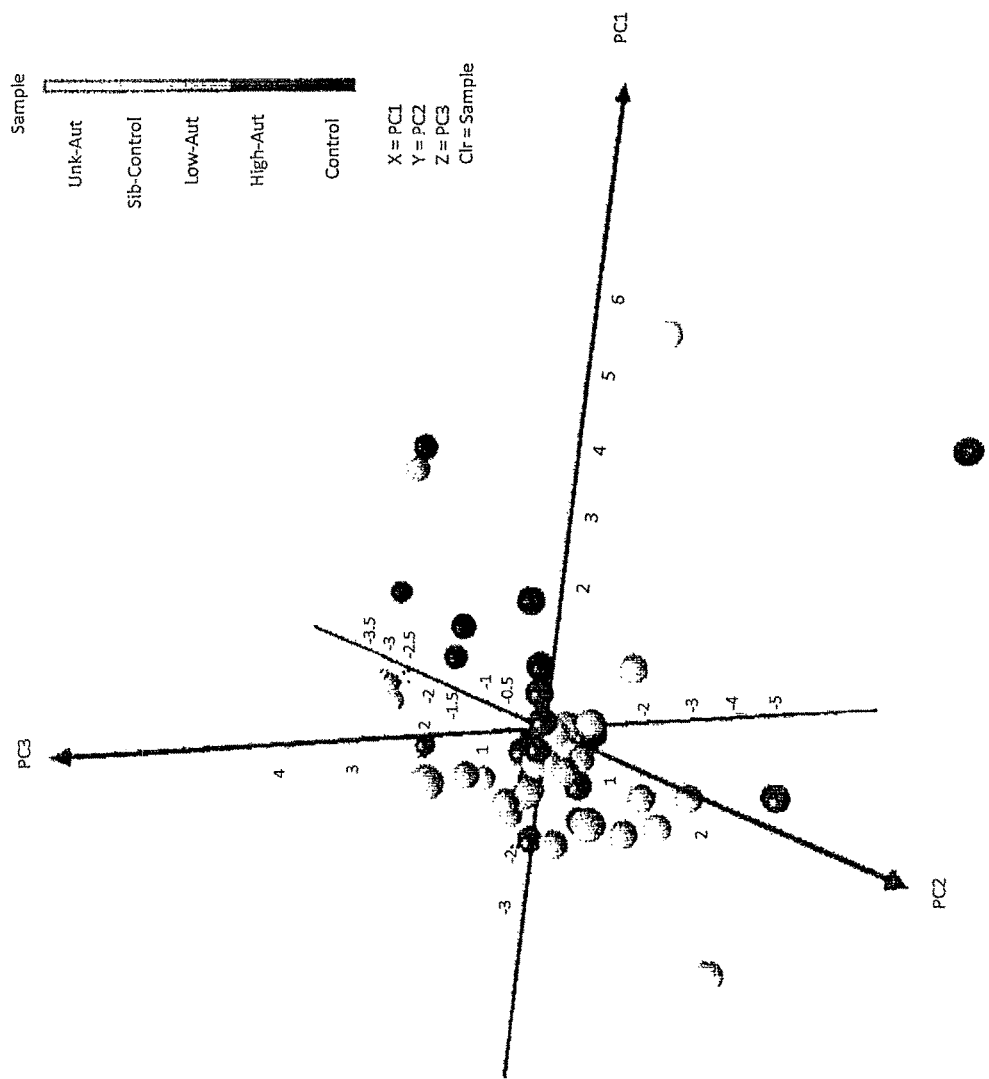
FIG. 2A shows the mapping according to the severity of the autism.
Figure 2B:
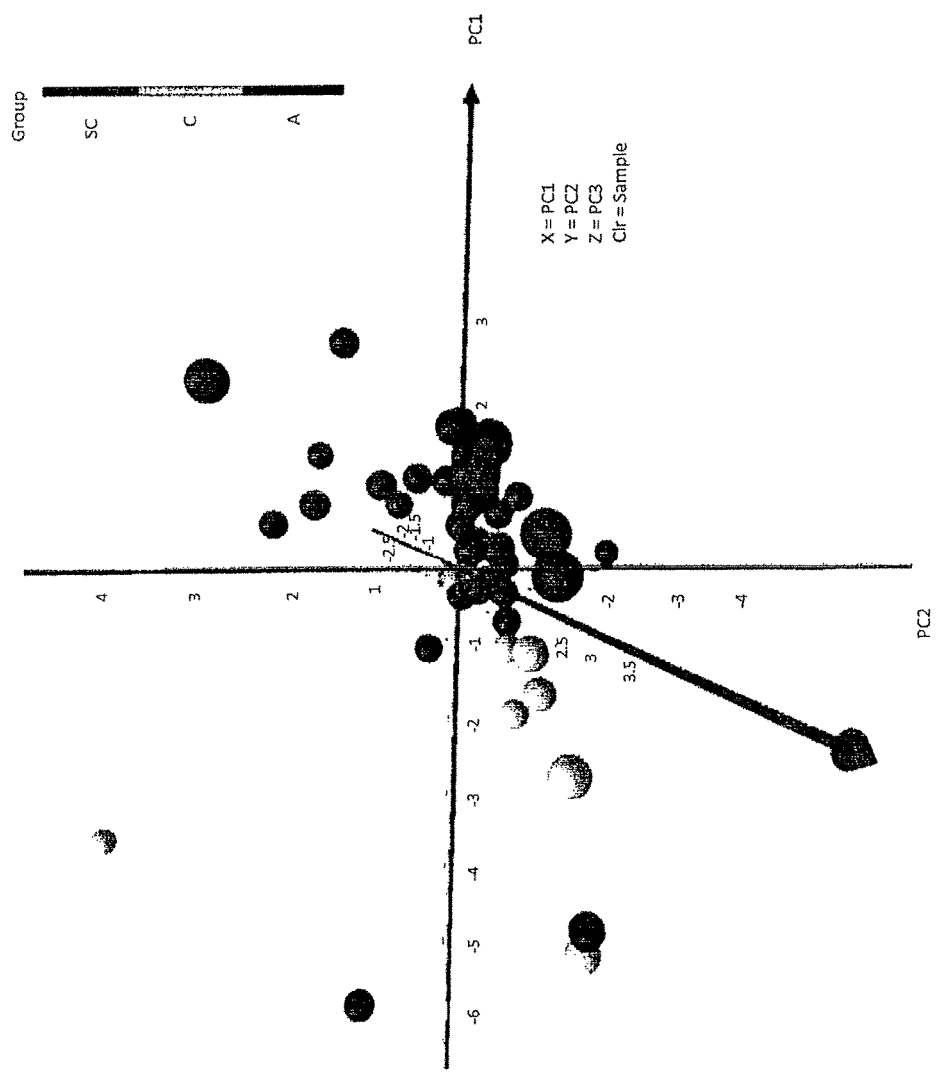
FIG. 2B shows phylum level mapping of the autistic children (A), control (C), and sibling (SC).

Using the phylum composition data to analyze the microbiome further, Principal Component Analysis was performed. The analysis incorporates 9 variables (the nine phyla represented in the samples). The data suggested the autistic and control individuals were separable based on the taxonomic percentages associated with each of the groups (FIG. 2A). FIG. 2A displays the mapping of all four classes at the phylum level and covers 60.935 percent of the variation. The image accentuates the difference of the control samples from the rest of the groups. While the control points are more scattered across the grid, the mild and severe autistic points, along with the siblings of autistic children tend to cluster together. This can be more clearly seen in FIG. 2B where all autistic samples are grouped under the same color. This supports the supposition that there is a difference in the fecal microflora between autistic and non-autistic children. Even children close to autistic individuals seem to possibly be influenced by the bacteria, and overall do not appear to be statistically different from children suffering from autistic symptoms.

Figure 3A:
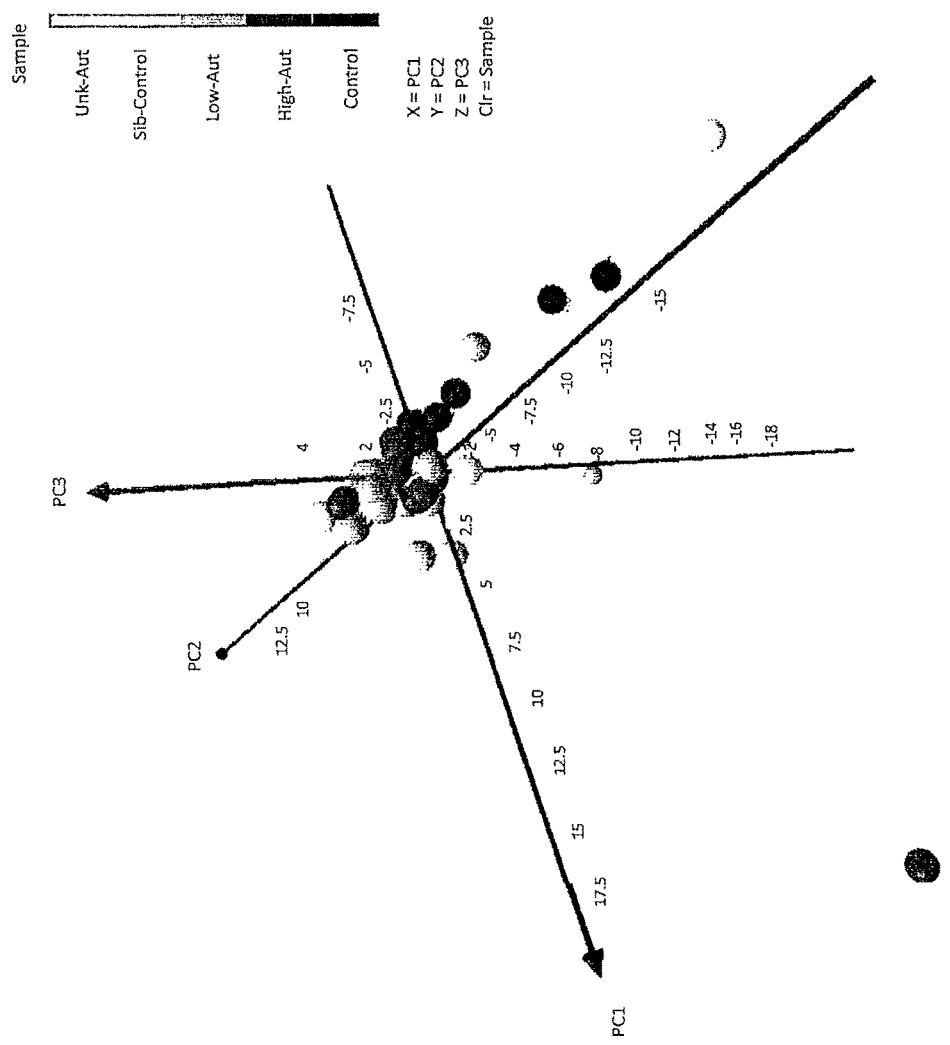
FIG. 3A shows the mapping according to severity of autism.
Figure 3B:
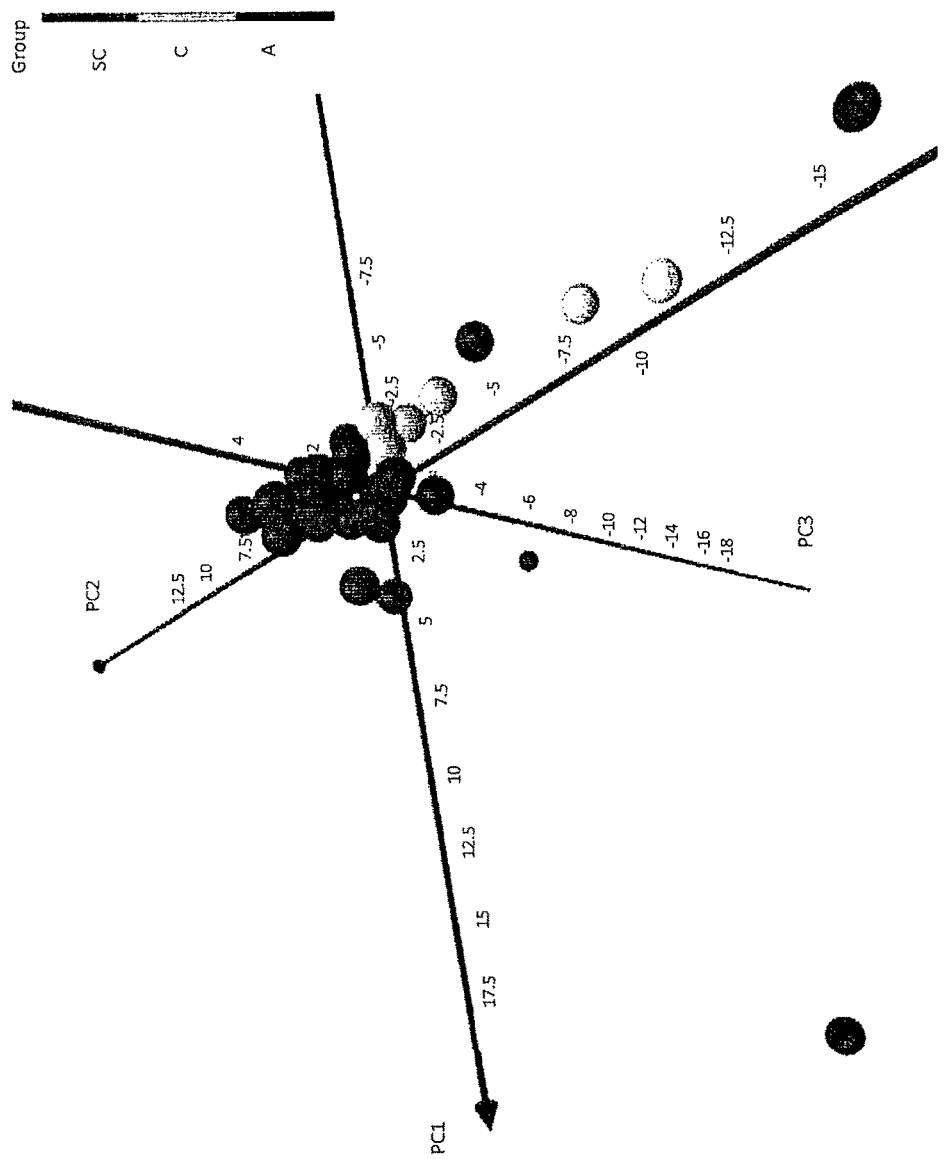
FIG. 3B shows genus level mapping of the autistic children (A), control (C), and sibling (SC).

A similar graphical pattern of separation for the four groups propagates through all taxonomic levels. In FIGS. 3A and 3B, the PCA results for the genus level (198 variables/genera used for analysis) can be seen. Although the dividing line was less obvious and the three principal components only covered 18.46% of the variation, the control samples remained distinguishable from the rest of the samples.

Another observation associated with abundance data at the genus level indicated that there are reduced populations of the *Bifidobacterium* genus in the severely autistic samples, compared with the controls. Evaluation of the *Bifidobacterium* genus-related data shows that there was a significantly higher occurrence of species among the control subjects than in the autistic subjects (p<0.05) and though not individually significant, the species were found at higher frequencies in the control subjects (Table 6).

TABLE 6

*Bifidobacterium* spp. quantities and significance levels within severely autistic and control samples (non sibling). *Bifidobacterium* species are listed in the "Species" column, along with the average percentage at which they were found in the autistic and control samples. These values are listed in the "Avg A" and "Avg C" columns for autistic and control samples, respectively, followed by their respective standard deviations listed in the "St. Dev" columns. A t-test based p-value is listed under the "p-value" column.

| Species | Avg A (n = 11) | St. Dev A | Avg C (n = 8) | St. Dev C | p-value |
|---|---|---|---|---|---|
| B. adolescentis | 0.125 | 0.261 | 0.154 | 0.384 | 0.424 |
| B. angulatum | 0.000 | 0.000 | 0.046 | 0.089 | 0.050 |
| B. animalis | 0.005 | 0.016 | 0.000 | 0.000 | 0.205 |
| B. bifidum | 0.012 | 0.020 | 0.017 | 0.048 | 0.372 |
| B. dentium | 0.001 | 0.005 | 0.000 | 0.000 | 0.205 |
| B. longum | 0.084 | 0.150 | 0.636 | 0.957 | 0.037 |
| B. pseudocatenulatum | 0.025 | 0.063 | 0.161 | 0.288 | 0.072 |
| B. pseudolongum | 0.000 | 0.000 | 0.012 | 0.034 | 0.126 |
| B. saeculare | 0.006 | 0.020 | 0.000 | 0.000 | 0.205 |
| Bifidobacterium genus | 0.258 | | 0.409 | | 0.258 |

*Bifidobacterium* along with *Lactobacillus* spp. are notable as probiotics, though little is known about strain specific differences, which may be host or individually specific (McCartney et al., *Life Sci.* 71, 1893-1904, 2002). Probiotic therapy to alleviate symptoms of gastrointestinal disorders has produced only slight or no improvement of such disease states. The use of probiotics in autism-related disorders has also been discussed though little clinical evidence is apparent for the efficacy of such treatment. Different species of *Bifidobacterium* produce different exopolysaccharides that act as fermentable substrates for different human intestinal bacteria.

Other genera of interest are listed in Table 7.

TABLE 7

Top 20 occurring genera out of 198 of severely autistic and control (non sibling) subjects. The number of samples the bacterial species were seen in is listed in the # A or #C columns. The average percentage (% Total Flora) designates the average percentage of the specific taxa found in the total microflora in the group of samples containing the genus (autistic or control).

| A, top 20 genera | # A (n = 11) | % Total Flora A | C, top 20 genera | # C (n = 8) | % Total Flora C |
|---|---|---|---|---|---|
| Bacteroides | 11 | 35.544 | Bacteroides | 8 | 24.481 |
| Clostridium | 11 | 10.343 | Clostridium | 8 | 17.748 |
| Faecalibacterium | 11 | 10.173 | Faecalibacterium | 8 | 11.271 |
| Eubacterium | 11 | 5.521 | Ruminococcus | 8 | 7.581 |
| Ruminococcus | 11 | 3.329 | Eubacterium | 8 | 9.749 |
| Roseburia | 11 | 2.033 | Alistipes | 8 | 2.621 |
| Dorea | 11 | 0.297 | Roseburia | 7 | 0.742 |
| Hespellia | 11 | 0.176 | Anaerofilum | 5 | 0.104 |
| Turicibacter | 11 | 0.152 | Streptococcus | 8 | 0.600 |
| Akkermansta | 10 | 7.344 | Turicibacter | 6 | 3.773 |
| Parabacteroides | 10 | 5.222 | Parabacteroides | 7 | 1.980 |
| Alistipes | 10 | 4.296 | Dorea | 8 | 3.504 |
| Sporobacter | 9 | 1.173 | Veillonella | 6 | 0.740 |
| Bifidobacterium | 9 | 0.258 | Akkermansia | 5 | 1.026 |
| Anaerostipes | 9 | 0.223 | Sporobacter | 1 | 0.054 |
| Ethanoligenens | 9 | 0.113 | Ethanoligenens | 6 | 0.477 |
| Anaerotruncus | 9 | 0.092 | Papillibacter | 5 | 0.140 |
| Holdemania | 9 | 0.084 | Holdemania | 6 | 0.107 |
| Phascolarctobacterium | 8 | 1.382 | Weissella | 4 | 1.918 |
| Desulfovibrio | 8 | 0.276 | Dialister | 3 | 0.032 |

In Table 7, the top 20 genera, of a total of 198 encountered, indicated a similar overall composition between the severely autistic and control groups. However, *Hespellia, Anaerostipes*, and *Desulfovibrio* spp. were seen in the top 20 genera only in the autistic subjects and *Streptococcus, Veillonella, Weissella*, and *Papillibacter* spp. were only in the control subjects among the top 20. The 19 genera with significant differences from this data include *Turicibacter, Clostridium, Weissella, Parabacteroides* and *Ruminoccocus* spp and others (Table 8).

TABLE 8

Significant genera among severely autistic vs non-sibling control samples. The number of samples of the specific bacterial genus found is listed in the "# of Autistic" or "# of Control", depending on which group the bacteria was found in exclusively. The average percent of bacteria found are in the column "Avg % A" or "Avg % C" for autistic or control samples, respectively; "0.000" indicates undetected. P-values are provided for comparisons of A vs C for each of the genera specified. A total of 198 genera were considered. Genera listed in bold are in the top 20 most predominant genera in extremely autistic or control groups (Table 7).

| Genus | # of Autistic (n = 11) | # of Control (n = 8) | avg % A | avg % C | p-val A vs C |
|---|---|---|---|---|---|
| Weissella | 0 | 6 | 0.000 | 0.095 | <0.001 |
| Turicibacter | 11 | 8 | 0.152 | 0.600 | <0.001 |
| Clostridium | 11 | 8 | 10.343 | 17.748 | 0.001 |
| Anaerofilum | 8 | 8 | 0.240 | 1.228 | 0.005 |
| Alkaliflexus | 8 | 0 | 0.122 | 0.000 | 0.006 |
| Pseudoramibacter | 5 | 5 | 0.027 | 0.132 | 0.011 |
| Desulfovibrio | 8 | 3 | 0.276 | 0.032 | 0.011 |
| Acetanaerobacterium | 8 | 1 | 0.083 | 0.005 | 0.015 |
| Ruminococcus | 11 | 8 | 3.329 | 9.749 | 0.018 |
| Strptococcus | 8 | 8 | 0.135 | 0.861 | 0.019 |
| Anaerovorax | 4 | 5 | 0.017 | 0.159 | 0.028 |
| Dialister | 4 | 5 | 0.090 | 4.691 | 0.035 |
| Lactococcus | 0 | 3 | 0.000 | 0.028 | 0.035 |
| Parabacteroides | 10 | 7 | 5.222 | 1.980 | 0.036 |
| Leuconostoc | 4 | 3 | 0.010 | 0.052 | 0.040 |
| Ethanoligenens | 9 | 6 | 0.113 | 0.477 | 0.041 |
| Bacteroides | 11 | 8 | 35.544 | 24.481 | 0.044 |
| Helcococcus | 0 | 2 | 0.000 | 0.011 | 0.045 |
| Alkaliphilus | 0 | 2 | 0.000 | 0.010 | 0.046 |

The mean differences for the other 179 genera were not significant. Table 9 shows the various genera and species detected among the Firmicutes and Bacteroidetes phyla.

TABLE 9

Genera and species present in greater than 1% of the total flora in one or more groups of children

|  | Autistic (No) | | Control (No) | |
| --- | --- | --- | --- | --- |
|  | Mild (22) | Severe (11) | Normal (8) | Sibling (7) |
|  | % of the total flora | | | |
| Firmicutes: | | | | |
| Clostridium aldenense | 1.9 | 1.7 | 1.7 | 0.6 |
| Clostridium hathewayi | 2.3 | 1.6 | 1.2 | 1.6 |
| Clostridium leptum | 0.2 | 0.4 | 2.7 | 0.1 |
| Clostridium methylpentosum | 0.3 | 0.1 | 1.6 | 0.2 |
| Clostridium orbiscindens | 1.8 | 1.7 | 1.3 | 0.6 |
| Dialister invisus | 0.6 | 0.1 | 4.7 | 1.1 |
| Eubacterium eligens | 1.9 | 3.0 | 0.6 | 1.7 |
| Eubacterium ruminantium | 0.2 | 0.1 | 1.7 | 1.4 |
| Phascolarctobacterium faecium | 1.5 | 1.4 | 1.9 | 2.2 |
| Roseburia intestinalis | 3.6 | 2.0 | 2.5 | 2.4 |
| Sporobacter termitidis | 1.0 | 1.2 | 0.7 | 1.5 |
| Bacteroidetes: | | | | |
| Alistipes onderdonkii | 1.2 | 1.19 | 1.4 | 0.5 |
| Bacteroides caccae | 1.7 | 0.5 | 4.9 | 0.9 |
| Bacteroides stercoris | 2.3 | 0.7 | 0.3 | 2.8 |
| Bacteroides vulgatus | 13 | 12 | 3.6 | 2.5 |
| Parabacteroides distasonis | 2.5 | 2.5 | 1.6 | 1.1 |
| Prevotella oulorum | 0.2 | 2.0 | 0 | 8.6 |

Tables 10 and 11 show genera and species of possible importance in contributing to the clinical picture of autism or as protective flora, respectively.

TABLE 10

Genera and species of possible importance in contributing to autism

|  | % of Total Flora | | |
| --- | --- | --- | --- |
|  | Severe Autism (11) | Control (8) | P Value |
| Desulfovibrio genus | 0.28 | 0.03 | 0.010 |
| Desulfovibrio piger | 0.11 | 0.006 | 0.032 |
| Desulfovibrio desulfuricans | 0.28 | 0 | 0.035 |
| Desulfovibrio intestinalis | 0.10 | 0.03 | 0.045 |
| Bacteroides vulgatus | 12.13 | 3.63 | 0.045 |

TABLE 11

Genera and species of possible importance as protective flora

|  | % of Total Flora | | |
| --- | --- | --- | --- |
|  | Severe Autism (11) | Control (8) | P Value |
| Collinsella genus | 0.02 | 0.62 | 0.050 |
| Bifidobacterium genus | 0.26 | 0.41 | 0.050 |
| Bifidobacterium longum | 0.08 | 0.64 | 0.037 |
| Bifidobacterium angulatum | 0 | 0.05 | 0.050 |
| Dialister invisus | 0.08 | 4.67 | 0.035 |
| Clostridium leptum | 0.35 | 2.70 | 0.010 |

Desulfovibrio was particularly interesting since all three species of this genus that were encountered showed significantly greater percentages of the total flora in the stools of severely autistic children than in controls. Furthermore, this sulfate-reducing genus has been recovered from serious infections such as bacteremia. This genus produces hydrogen sulfide, an important virulence factor, and is known to corrode various metals. It might have the opportunity to attack certain metals in the bowel.

Figure 4:
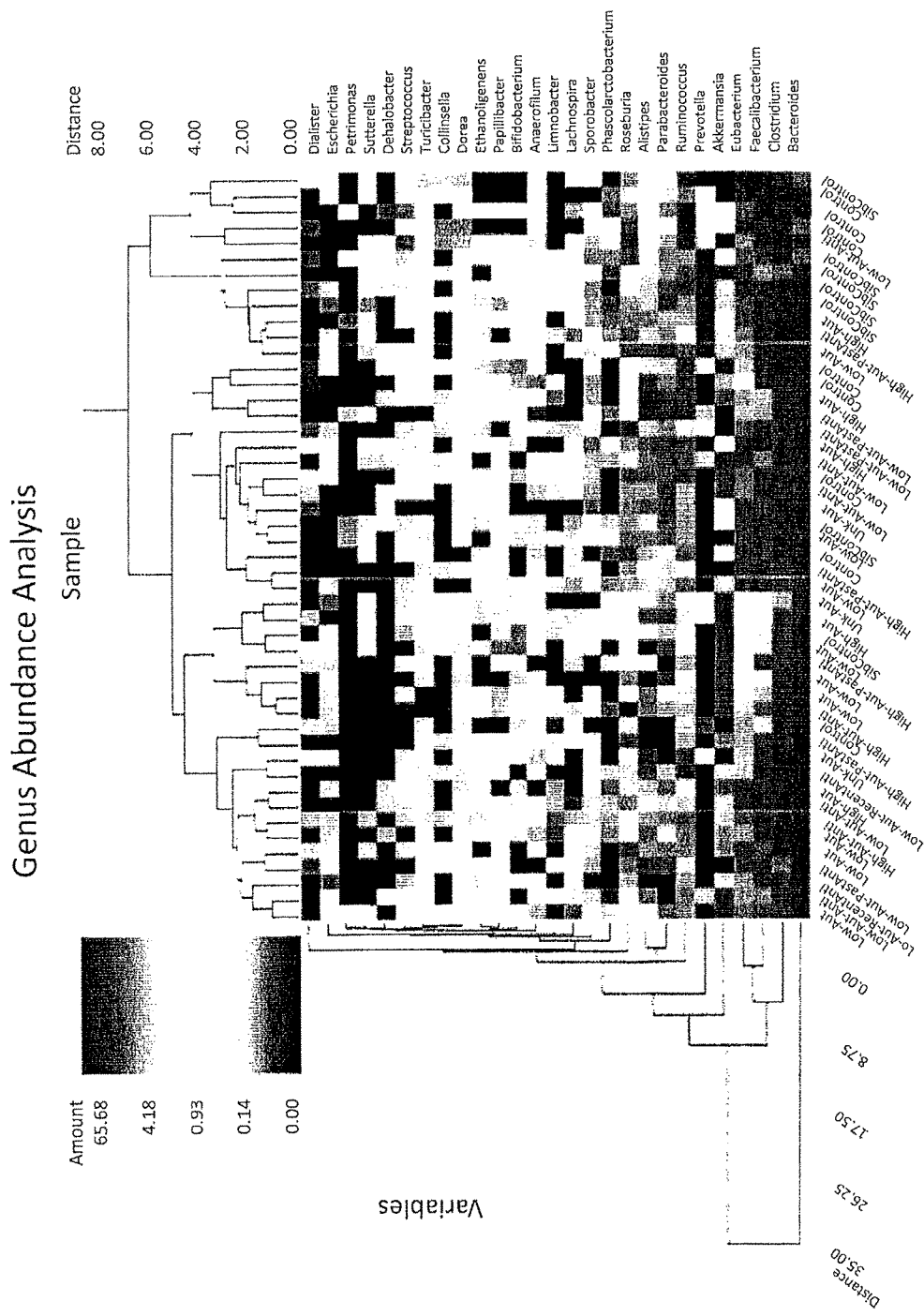
FIG. 4 is a map of the genus abundance analysis.

Using the overall predominant genera, clustering analysis was performed to assess the importance of the bacterial gut flora of autistic children and the control and sibling control subjects. FIG. 4 shows the results of a clustering of all samples. Starting with the 198 genera, the number of genera was reduced until there was a change in the clustering. Thus only 27 of the 198 genera are needed to display the clustering patterns. The left and right sides of the double dendrogram show some indication of grouping. In the left portion of the image, the mildly autistic samples group together on the far left and other severity levels of autism further to the right. The far right portion of the dendrogram is primarily composed of the control and sibling control individuals. Based on this information, there appears to be some indication of the gut microflora differing between the autistic and control groups. The Bacteroides genus, in particular, is an obvious indication of the change that occurs from autistic to sibling and control children. The red color (bottom of FIG. 4), indicating a high abundance of the genus regresses to more orange and yellow tones (center of FIG. 4) indicating a decrease in the amount of the bacteria Example 5

Materials and Methods

Study Design

The study is limited to autistic children with late onset or regressive autism and gastrointestinal (GI) abnormalities, notably abdominal pain or discomfort, bloating, and constipation with or without diarrhea. We used the stool samples from our pyrosequencing study[12], maintained at −80° C., and employed real-time PCR and culture to study the incidence of Desulfovibrio in autism and controls and to recover Desulfovibrio strains to study further. We did not use three of the autistic subjects' stools because two had Asperger's syndrome and one was an adult. We also added four additional healthy controls.

Subjects

The stool specimens were from 30 regressive autistic subjects, 23 males and 7 females, with GI symptomatology (primarily constipation with or without "compensatory" diarrhea but abdominal distension or discomfort/pain were also common), 7 healthy siblings (5 females and 2 males), and 12 healthy controls (7 males and 5 females, ages 4-10 years) having no contact with autistic children. Ages ranged from 2 to 13 years. Eleven of the autistic subjects had severe to moderately severe symptoms and 19 had mild disease. The autistic subjects and their siblings were from the practice of John Green, M.D. in Evergreen, Oreg. All subjects there had an educational or developmental pediatrician evaluation. Subsequently, Dr. Green evaluated each patient and validated the diagnosis of autism based on impairment in social skills, impairment in language skills and verbal communication, sensory disturbances, repetitive stereotypical behaviors, and gastrointestinal disturbances. Dr. Green's practice has been limited to autistic spectrum disorders since 1999 and he has evaluated and treated some 2,000 patients in that time. The twelve control subjects were from the Los Angeles area and other areas served by CARD and were children of administrative personnel who worked at the Center for Autism and Related Disorders (CARD) but not on floors where patients were seen. There were 7 males and 5 females and ages ranged from four to ten years. The study was approved by IRBs at the two collaborating institutions and at the VA Medical Center in Los Angeles. Subjects were excluded if they had been on any antibacterial agents or probiotics within the past month. It wasn't possible to get the parents to agree to discontinue antifungal agents (which possibly have some antibacterial activity as well) and it wasn't possible to standardize diet for all subjects.

Stool Collection, Storage, and Initial Processing

Specimens (the entire bowel movement because bacteria are distributed randomly in feces) were collected at the homes of the children and were shipped to the Wadsworth Va. Anaerobe Laboratory the same day, in styrofoam boxes with frozen shipping packets. Specimens always arrived at the laboratory the next morning. They were homogenized inside an anaerobic chamber, DNA extracted, and cultures set up. Data was corrected to dry weight.

Blinding of Subject Information

Subject identification was withheld from all investigators doing laboratory studies. Identification of type of patient (autism vs. the two control groups) was withheld from laboratories involved until the data was collected; it was then released for data analysis.

DNA Extraction

DNA was extracted using a commercial system (QIAamp DNA stool mini kit; Qiagen) according to manufacturer's instructions. Our laboratory studies have shown that this product produces high-quality DNA free of PCR-inhibiting substances.

Real-Time PCR

The real-time PCR procedure used is described in an earlier publication[30]. Oligonucleotide primers and probes were designed (see Table 12). Standard curves were constructed to enumerate the Desulfovibrio species using the 7500 Real-Time PCR System (Applied Biosystems).

dilutions of each specimen, and examined at intervals for 10 days. Black colonies were studied by 16S rRNA sequencing[31] for identification.

Antimicrobial Susceptibility Testing

The Clinical and Laboratory Standards Institute (CLSI) protocol was used in a serial two-fold plate dilution procedure[32] employing 25 strains of Desulfovibrio isolated from stools or clinical specimens plus two type strains, as noted, and the standard reference strains (Bacteroides thetaiotaomicron and Bacteroides fragilis) and seven antimicrobial agents. The production of β-lactamase was detected by the nitrocefin disk test[33].

Statistical Analysis

The maximum of the four culture values for any sample (D. piger, D. fairfieldensis, D. desulfuricans, and Desulfovibrio species) was taken as the final "culture" outcome. Similarly, the maximum of the three real-time-PCR values (D. piger, D. fairfieldensis, D. species) was taken as the final RT-PCR value. Any response not recorded as "zero" (i.e., below the threshold of detection) is considered positive. Values recorded as zero (below the level of detection) are negative.

In addition to reporting observed agreement between the culture and RT-PCR assessments for the presence or absence of Desulfovibrio species, the Kappa statistic was computed to correct for chance agreement. Kappa is near zero if the agreement is only due to chance.

The p values for comparing proportions between different groups were computed using Fishers exact test or the chi-square test for overall comparisons. Trends in proportions were computed using the Cochran-Armitage method.

Since all of the control values, all but one or two of the sib control values and a majority of the autism values are "zero" for culture and RT-PCR, mean comparisons were not carried out.

Results

Culture and Real-Time PCR.

Stools were obtained from 30 autistic subjects, 7 siblings of these children, and 12 healthy controls, a total of 49

TABLE 12

Sequences of oligonucleotide primers and probes

| Target organism | $T_m$ | Target gene | Forward primer (5'-3') | Reverse primer (5'-3') | Probe (5'-3') |
|---|---|---|---|---|---|
| D. desulfuricans | 60 | 16S rRNA | GGATCGTAAACCTCTGTC CTTTACGCCCAGTAG | (G/A) ATTCC AACTACGTTGTGCTAATCAGCA GCGT | |
| D. fairfieldensis | 53 | 16S rRNA | GGACTCATCCTCATACGA TCGAGTAGAGTGGCGCA CA | | GCAAGCAGAGGCCGTCTTTCCC CT |
| D. intestinalis | 60 | 16S rRNA | GGATCGTAAACCTCTGTC CTTTACGCCCAGTAG | (G/A) ATTCC AGAAACCGCACCGTGCTAATC AGCG | |
| D. piger | 60 | 16S rRNA | GGATCGTAAACCTCTGTC CTTTACGCCCAGTAG | (G/A) ATTCC AAGAAACTAGGGTGTTCTAATC ATCATCC | |
| D. vulgaris | 60 | 16S rRNA | GGATCGTAAACCTCTGTC CTTTACGCCCAGTAG | (G/A) ATTCC CGGTGCTAATCAGCCGTGGTCT G | |
| Desulfovibrio spp. | | 16S rRNA | CCGTAGATATCTGGAGG AACATCAG | ACATCTAGCATCCATCGTTTAC AGC | |

Culture

A selective and differential medium was designed consisting of Brucella agar with ferric ammonium citrate 0.05%, pyruvate 1%, $MgSO_4$ 0.25%, and vancomycin 10 μg/ml. Plates were inoculated with 10 μl/plate of serial ten-fold specimens studied. The results of the culture and real-time PCR, with statistical analysis, are given in Tables 13A, 13B, 13C, and 13D. Fourteen of the stool specimens from 30 autistic children were positive for Desulfovibrio by culture or real-time PCR (46.7%) compared to two stools of seven from siblings of autistic children (28.6%) and zero of 12 stools from healthy controls not exposed to autism. Severity was arbitrarily graded from 4 (most severe) to 1 (least severe) based on Dr. Green's clinical judgment and 0 for no autism. The more severe the autism the higher the percent positive by either culture or real-time PCR; the numbers are small but the dose response was consistent. Overall, there were 13 specimens positive by culture and 9 by real-time PCR; the overall agreement between methods was significant (p=0.005). The combination of both methods increased the overall yield to 16 positives in the 49 specimens studied, compared to 13 positive by culture and 9 by real-time PCR. The specificity was relatively good (90%), but the sensitivity was only 47%. The odds ratio was 7.44.

TABLE 13A

Overall agreement between culture versus RT-PCR in n = 49 subjects

|  | RT-PCR Neg | RT-PCR Pos | Total |
| --- | --- | --- | --- |
| Culture Neg | 33 | 3 | 36 |
| Culture Pos | 7 | 6 | 13 |
| Total | 40 | 9 | 49 |

Observed agreement = (33 + 6)/49 = 79.6%,
Kappa = 0.419 +/− 0.150, p = 0.005

TABLE 13B

Percent positive by culture OR RT-PCR

| Group | N | Num pos | Pct pos | SE |
| --- | --- | --- | --- | --- |
| Autism | 30 | 14 | 46.7% | 9.1% |
| Control | 12 | 0 | 0% | — |
| Sib control | 7 | 2 | 28.6% | 17.1% |
| Total | 49 | 16 | 32.6% | 6.7% |

Overall chi square = 8.55, p value = 0.014

TABLE 13B-continued

| Comparison | p value |
| --- | --- |
| Autism vs control | 0.003 |
| Autism vs sib | 0.675 |
| Control vs sib | 0.123 |

TABLE 13C

Autism severity vs percent positive by culture OR RT-PCR

| Severity | n | Num pos | Pct pos | SE |
| --- | --- | --- | --- | --- |
| 0 (no autism) | 19 | 2 | 10.5% | 7.0% |
| 1 | 6 | 2 | 33.3% | 19.2% |
| 2 | 9 | 4 | 44.4% | 16.6% |
| 3 | 7 | 3 | 42.9% | 18.7% |
| 4 | 4 | 2 | 50.0% | 25.0% |
| >=1* | 4 | 3 | 75.0% | 21.7% |
| Total | 49 | 16 | 32.6% | 6.7% |

*not used in trend p value calculation since actual severity unknown
Trend Z = −2.23,
p value = 0.03

TABLE 13D

Sensitivity and specificity using culture OR RT-PCR
Positive if EITHER is positive, Negative if BOTH are negative
Combining controls and sib controls

|  | autism | control | Total |
| --- | --- | --- | --- |
| Test pos | 14 | 2 | 16 |
| Test neg | 16 | 17 | 33 |
| Total | 30 | 19 | 49 |

Sensitivity = 14/30 = 47% ± 9%
Specificity = 17/19 = 90% ± 7%
Unweighted Accuracy = (Sensitivity + Specificity)/2 = 68% ± 6%. Odds ratio 7.44

Antimicrobial Susceptibility.

The susceptibility of *Desulfovibrio* species to seven antimicrobial compounds is shown in Table 14. The ten strains tested all produced β-lactamase.

TABLE 14

Antimicrobial susceptibility patterns of *Desulfovibrio* (MIC, mcg/ml)

|  |  | Aztreonam | Azt + Clav | Colistin | Kanamycin | Polymyxin B | TMX/Sul | Vancomycin |
| --- | --- | --- | --- | --- | --- | --- | --- | --- |
| 1 | 8236 | 256 | 16 | >512 | 512 | 256 |  | 256 |
| 2 | 8381 | 128 | 16 | >512 | 256 | >512 | 256 | >512 |
| 3 | 8907 | 256 | 16 | >512 | 256 | >512 | 512 | >512 |
| 4 | 8933 | 256 | 8 | >512 | 512 | >512 | 256 | >512 |
| 5 | 8951 | 64 | 16 | >512 | 512 | >512 | 256 | >512 |
| 6 | 9070 | 512 | 16 | >512 | 512 | >512 | >512 | >512 |
| 7 | 9120 | 256 | 32 | >512 | 256 | >512 | 256 | >512 |
| 8 | 9706 | 256 | 32 | >512 | 256 | >512 | 256 | >512 |
| 9 | 9976 | 256 | 8 | >512 | 128 | >512 | 256 | 512 |
| 10 | 10831 | 256 | 4 | >512 | 256 | 128 |  | 256 |
| 11 | 11081 | 256 | 8 | >512 | 512 | 256 |  | 256 |
| 12 | 11094 | 256 | 8 | >512 | 512 | 256 |  | >512 |
| 13 | 11232 | 64 | 8 | >512 | 256 | >512 | 128 | >512 |
| 14 | 11346 | 256 | 16 | >512 | 512 | >512 | 512 | >512 |
| 15 | 11378 | 256 | 8 | >512 | 512 | 256 |  | 256 |
| 16 | 11437 | 64 | 16 | >512 | 128 | >512 | 4 | >512 |
| 17 | 11568 | 256 | 8 | >512 | 512 | >512 | >512 | >512 |
| 18 | 11623 | 256 | 16 | >512 | 256 | >512 | 512 | >512 |
| 19 | 11717 | 256 | 8 | >512 | 512 | 256 |  | >512 |
| 20 | 11789 | 32 | 8 | >512 | 256 | 16 |  | >512 |
| 21 | 11830 | 64 | 4 | >512 | 128 | 128 |  | >512 |
| 22 | 11949 | 256 | 8 | >512 | 128 | >512 | 512 | >512 |

TABLE 14-continued

Antimicrobial susceptibility patterns of *Desulfovibrio* (MIC, mcg/ml)

|    |         | Aztreonam | Azt + Clav | Colistin | Kanamycin | Polymyxin B | TMX/Sul | Vancomycin |
|----|---------|-----------|------------|----------|-----------|-------------|---------|------------|
| 23 | 12379   | 16        | 4          | >512     | 512       | 8           |         | 256        |
| 24 | 13966   | 24        | 16         | >512     | 512       | >512        | 512     | >512       |
| 25 | 4019    | 512       | 8          | >512     | 512       | 256         |         | >512       |
| 26 | $7757^T$ | 256      | 64         | >512     | 512       | 256         | >512    | >512       |
| 27 | $29098^T$ | 32     | 64         | >512     | 128       | 256         | 256     | 1          |

Discussion

There are 220 species of sulfate-reducing bacteria in 60 genera.[14] Only the genus *Desulfovibrio* appears to be associated with autism although other genera such as *Clostridium* that contain some sulfate reducers or that might act in other ways additively or synergistically with *Desulfovibrio* should be studied. *Desulfovibrio* is an anaerobic gram-negative non-spore-forming short rod, usually curved and rapidly motile by means of a single polar flagellum (except for *D. piger*). Black ($H_2S$), pinpoint colonies or black confluent growth, may appear in 3 days of anaerobic incubation on appropriate media. Colonies may continue to appear up to about 10 days of continued incubation. The five species of *Desulfovibrio* found in humans are *D. desullitricans, D. fairfieldensis, D. piger, D. intestinalis*, and *D. vulgaris*. The incidence of *Desulfovibrio* in human bowel flora varies in different countries, perhaps related to diet and age[15]. The organisms were not only in feces; they colonized the gut wall in rectal biopsies, with counts of $10^6$-$10^7$. The low incidence in our control group suggests that it is uncommon in young children in the U.S. The fact that the stools from siblings were in between the autism and control stools for *Desulfovibrio* positivity by either culture or real-time PCR suggests the possibility of exposure of the siblings to the organism, although the numbers are small. However, the trend was significant (p=0.03).

Our proposed pathogenesis of regressive autism with GI manifestations is shown in FIG. 5. Genetic background and environmental contamination with toxic substances can damage the immunologic capabilities of young children, predisposing them to autism. There may be exposure to *Desulfovibrio* from contact with other children who are autistic, or from the environment (soil; foods; surfaces, fomites in the home.). Diet is important in determining the intestinal microbiome. The final insult may be exposure to antimicrobial compounds (probably primarily oral cephalosporins) administered for ear or other infections. Niehus and Lord (20) reviewed medical records from birth to age 2 years of 99 children (75 who developed ASD, 29 who had regressive disease, and 24 who developed normally). Children who developed autism had significantly more ear infections and were given significantly more antibiotics than those who developed normally. *Desulfovibrio* is often resistant to cephalosporins which suppress certain elements of the indigenous bowel flora and thus permit outgrowth of *Desulfovibrio*. Also, various beta-lactam antibiotics inhibit the mitochondrial carnitine/acylcarnitine transporter[16]. Antibiotics of all types also release LPS from bacteria[17].

The onset of regressive autism in relation to use of antibiotics is reminiscent of antimicrobial use promoting *Clostridium difficile* infection in predisposed elderly persons in intensive care units in hospitals, or in nursing homes. Note also the parallel with infant botulism in which *Clostridium botulinum* (from soil, corn syrup, or honey) colonizes the gastrointestinal tract of infants whose bowel flora is not yet fully developed[18]. Antibiotics may also play a role in older children and even adults in colonization of the gut with *C. botulinum* and subsequent clinical botulism. In our earlier studies, we were impressed with the possibility of involvement of clostridia, notably the *C. clostridioforme* "group", in autism[19] but our recent pyrosequencing study[12] which included a larger number of autistic children and controls and permitted much more extensive detection of bowel flora elements indicated these clostridia were not prominent in autism and suggested that *Desulfovibrio* might be. One other organism, *Bacteroides vulgatus*, also had a significantly higher percent of the total flora in the autistic subjects than in the controls in the pyrosequencing study[12] but real-time PCR studies indicated that the differences were really not significant. The pyrosequencing study also demonstrated some bacteria that were potentially protective (higher percent of the total flora in control subjects than in the autistics), particularly bifidobacteria. This requires further study. Although *Desulfovibrio* does not produce spores, it has several mechanisms making it resistant to oxygenation and able to survive other deleterious encounters[20]. The physiology and metabolism of *Desulfovibrio* position it uniquely to account for much of the pathophysiology seen in autistic children.

Lipopolysaccharide (LPS) has been noted in *Desulfovibrio*[21] and by Dr. Beenhouwer of our group. Emanuele et al. showed that serum levels of endotoxin were significantly higher in autistic subjects than in healthy ones and inversely and independently correlated with socialization[22].

*Desulfovibrio* produces hydrogen sulfide which is genotoxic and, at higher concentrations, cytotoxic to the colonic epithelium. $H_2S$ may also create cellular energy deficiency by inhibiting the β-oxidation of butyrate[23]. *Desulfovibrio* competes effectively with butyrate-producing bacteria for lactate, an important electron donor for sulfate reduction by *Desulfovibrio*. Interestingly, some sulfate-reducing bacteria carry out a propionic acid fermentation of lactate, converting 3 molecules of lactate to 2 of propionate; MacFabe et al. found that intracerebral injection of propionic acid or other short-chain fatty acids in rats led to biologic, chemical, and pathologic changes characteristic of autism[13]. Sulfide can also be derived from sulfur compounds in the diet or from endogenous mucins which are sulfated glycoproteins; this leads to vulnerability of the colonic epithelium. $H_2S$ is inhibitory to mitochondrial cytochrome c oxidase. The corrosive activity of hydrogen sulfide on metals, an important environmental problem, may have a counterpart in human health in consequence of the importance of certain metals in human metabolism. Hydrogen sulfide penetrates membranes readily and is likely to penetrate colonic epithelial cells and beyond, influencing local blood flow, immune function and neural reflex activity. Dr. Emma Allen-Vercoe offers an intriguing suggestion of a trial of 5-ASA to inhibit sulfidogenesis by *Desulfovibrio*.

James et al. present an excellent study of the normal methionine cycle, methylation and transsulfuration and abnormalities seen in 20 autistic children (19 of whom had "regressive" autism) as compared to results in 33 control children[24]. Waring and her colleagues in the United Kingdom have also been interested in sulfur metabolism in autism[25]. An important paper published recently by Yap et al. described results of urinary metabolic phenotyping using $^1$H NMR spectroscopy[26]. Perturbation of sulfur and amino acid metabolism was noted in autistic subjects vs. controls and there were also abnormalities in the tryptophan-nicotinic acid metabolic pathway. An increased demand for methylation of nicotinic acid to its N-methylated acid and amide, as seen in this study, would produce more stress on the compromised methylation capacity of autistic children and would lead to increased oxidative stress.

Aztreonam, kanamycin, gentamicin and other aminoglycosides, and vancomycin are virtually unabsorbed when given by the oral route. The same is true for colistin and polymyxin B, but these compounds do not penetrate the intestinal mucosa and this could be a problem for eradication of *Desulfovibrio* which can attach to the bowel mucosa[15]. The drugs that are not absorbed to any extent when given orally achieve very high levels in the bowel; this is important in interpreting the data in Table 14. Also important to note is the fact that aztreonam is a beta lactam compound and thus is susceptible to inactivation by beta-lactamases produced by *Desulfovibrio* as well as by many other components of the intestinal flora[27]. This can be overcome by giving aztreonam together with a beta-lactamase inactivator such as clavulanic acid (which resulted in much lower minimal inhibitory concentrations [MICs]. The potential toxicity of colistin, polymyxin, and kanamycin would mitigate against their use, given the availability of other options. Trimethoprim/sulfamethoxazole is absorbed well on oral administration so gut levels would likely be low which may be why this compound predisposes to autism, according to anecdotal reports. Vancomycin was included because of our positive experience with the oral form in an open label trial of regressive autism[9]. The drug is not very active on a weight basis, but it must be remembered that fecal levels of vancomycin are often 2-5,000 mcg/gm after oral administration.

Among other data on antimicrobial susceptibility of *Desulfobvibrio* are reports that it has been recovered from various infections, some serious[27-29].

REFERENCE LIST FOR EXAMPLE 5

1. Postgate J R. The sulphate-reducing bacteria. Cambridge: Cambridge University Press; 1979.
2. Hollander E, Anagnostou E. Clinical manual for the treatment of autism. Arlington, Va.: American Psychiatric Publishing; 2007.
3. Rimland B. The autism epidemic, vaccinations, and mercury. J Nutr Environ Med 2000; 10:261-266.
4. Pinto D, Pagnamenta A T, Klei L, Anney R, Merico D, Regan R. Functional impact of global rare copy number variation in autism spectrum disorders. Nature 2010.
5. Herbert M R, Russo J P, Yang S et al. Autism and environmental genomics. Neurotoxicology 2006; 27(5): 671-684.
6. Centers for Disease Control. Autism and developmental disabilities monitoring (ADDM) network. 0, 2010 http://www.cdc.gov/ncbddd/autism/addm.html).
7. HSPH. Autism has high costs to U.S. society. 0, 2006 http://www.hsph.harvard.edu/news/press-releases/2006-releases/press04252006.html).
8. IACC. Strategic plan for Autism Spectrum Disorder Research. 0, 2008 www.nimh.nih.gov/research-funding/scientific-meetings/recurring-meetings/iacc/strategic-plan/index.shtml).
9. Sandler R H, Finegold S M, Bolte E R et al. Short-term benefit from oral vancomycin treatment of regressive-onset autism. J Child Neurol 2000; 15(7):429-435.
10. Finegold S M, Molitoris D, Song Y et al. Gastrointestinal microflora studies in late-onset autism. Clin Infect Dis 2002; 35 (Suppl. 1):S6-S16.
11. Parracho H M, Bingham M O, Gibson G R, McCartney A L. Differences between the gut microflora of children with autistic spectrum disorders and that of healthy children. J Med Microbiol 2005; 54(Pt 10):987-991.
12. Finegold S M, Dowd S R, Gontcharova V et al. Pyrosequencing study of fecal microflora of autistic and control children. Anaerobe 2010; 16:444-453.
13. MacFabe D F, Cain D P, Rodriguez-Capote K et al. Neurobiological effects of intraventricular propionic acid in rats: possible role of short chain fatty acids on the pathogenesis and characteristics of autism spectrum disorders. Behav Brain Res 2007; 176(1):149-169.
14. Barton L L, Fauque G D. Biochemistry, physiology and biotechnology of sulfate-reducing bacteria. In: Laskin A I, Gadd G M, Sariaslani S, editors. Advances in Applied Microbiology. Amsterdam: Elsevier; 2009:41-98.
15. Macfarlane G T, Cummings J H, Macfarlane S. Sulphate-reducing bacteria and the human large intestine. In: Barton L L, Hamilton W A, editors. Sulphate-reducing bacteria. Cambridge: Cambridge University Press; 2007: 503-521.
16. Pochini L, Galluccio M, Scumaci D et al. Interaction of beta-lactam antibiotics with the mitochondrial carnitine/acylcarnitine transporter. Chem Biol Interact 2008; 173 (3):187-194.
17. Walters S M, Dubey V S, Jeffrey N R, Dixon D R. Antibiotic-induced *P. gingivalis* LPS release and inhibition of LPS-stimulated cytokines by antimicrobial peptides. Peptides 2010.
18. Shapiro R L, Hatheway C, Swerdlow D L. Botulism in the United States: A clinical and epidemiological review. Ann Intern Med 1998; 129(3):221-228.
19. Finegold S M. Therapy and epidemiology of autism—clostridial spores as key elements. Med Hypotheses 2008; 70(3):508-511.
20. Sass H, Cypionka H. Response of sulphate-reducing bacteria to oxygen. In: Barton L L, Hamilton W A, editors. Sulphate-reducing bacteria. Cambridge: Cambridge University Press; 2007:167-183.
21. Weglarz L, Wawszczyk J, Orchel A, Jaworska-Kik M, Dzierzewicz Z. Phytic acid modulates in vitro IL-8 and IL-6 release from colonic epithelial cells stimulated with LPS and IL-1beta. Dig Dis Sci 2007; 52(1):93-102.
22. Emanuele E, Orsi P, Boso M et al. Low-grade endotoxemia in patients with severe autism. Neurosci Lett 2010; 471(3):162-165.
23. Marquet P, Duncan S H, Chassard C, Bernalier-Donadille A, Flint H J. Lactate has the potential to promote hydrogen sulphide formation in the human colon. FEMS Microbiol Lett 2009; 299(2):128-134.
24. James S J, Cutler P, Melnyk S et al. Metabolic biomarkers of increased oxidative stress and impaired methylation capacity in children with autism. Am J Clin Nutr 2004; 80(6):1611-1617.

25. Waring R H, Klovrza L V. Sulphur metabolism in autism. J Nutr Environ Med 2000; 10:25-32.
26. Yap I K, Angley M, Veselkov K A, Holmes E, Lindon J C, Nicholson J K. Urinary Metabolic Phenotyping Differentiates Children with Autism from Their Unaffected Siblings and Age-Matched Controls. J Proteome Res 2010.
27. Nakao K I, Tanaka K, Ichiishi S, Mikamo H, Shibata T, Watanabe K. Susceptibilities of 23 human *Desulfovibrio* isolates. Antimicrob Agents Chemother 2009.
28. Welling G W, Groen G, Welling-Wester S, de Vries-Hospers H G, van der Waaij D. Enzymatic inactivation of aztreonam by faecal enzyme preparations from healthy volunteers. Infection 1987; 15(3):188-191.
29. Finegold S M, Molitoris D, Vaisanen M L. Study of the in vitro activities of rifaximin and comparator agents against 536 anaerobic intestinal bacteria from the perspective of potential utility in pathology involving bowel flora. Antimicrob Agents Chemother 2009; 53(1):281-286.
30. Song Y, Liu C, Finegold S M. Real-time PCR quantitation of clostridia in feces of autistic children. Appl Environ Microbiol 2004; 70(11):6459-6465.
31. Summanen P H, Lawson P A, Finegold S M. *Porphyromonas bennonis* sp. nov., isolated from human clinical specimens. Int J Syst Evol Microbiol 2009; 59:1727-1732.
32. Hecht D W, Citron D M, Cox M, Jacobus N, et al. Methods for Antimicrobial Susceptibility Testing of Anaerobic Bacteria; Approved Standard—Seventh Edition. 7 ed. Wayne, Pa.: Clinical and Laboratory Standards Institute; 2007.
33. Jousimies-Somer H R, Summanen P, Citron D, Baron E, Wexler H M, Finegold S. M. Wadsworth-KTL Anaerobic Bacteriology Manual. 6 ed. Belmont: Star Publishing; 2002.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method of treating autism associated with *Desulfovibrio* overgrowth in the gastrointestinal tract of a patient, said method comprising administering to the patient suffering from said autism a treatment course of aztreonam in an amount effective to treat autism in the patient, thereby treating autism.

2. The method of claim 1, further comprising administering a beta-lactamase inhibitor.

3. The method of claim 2, wherein the beta-lactamase inhibitor is selected from the group consisting of clavulanic acid, tazobactam, sulbactam and LK-157 or others.

4. The method of claim 1, wherein aztreonam and the beta-lactamase inhibitor are administered concurrently.

5. The method of claim 1 further comprising administering a probiotic and/or a probiotic group.

6. The method of claim 5, wherein the probiotic and/or a probiotic group is selected from the group consisting of bacteria that competes with *Desulfovibrio* for nutrients in the intestinal tract and bacteria that inhibits growth of *Desulfovibrio* in the intestinal tract.

7. The method of claim 5, wherein a probiotic and/or a probiotic group is selected from the group consisting of *Bacteroides thetaiotaomicron, Bacteroides vulgatus, Bacteroides distasonis, Bacteroides fragilis, Bifidobacterium adolescentis* group, *Eubacterium aerofaciens, Clostridium ramosum, Escherichia coli, Streptococcus faecalis* group, *Lactobacillus* spp., *L. acidophilus*, gram-negative anaerobes, enterococci, *Bacteroides* sp., *Parabacteroides, Prevotella, Porphyromonas*, gram-positive anaerobic cocci, *Clostridium* sp., Enterobacteriaceae, *E. coli, L. bulgaricus, S. thermophilus, Collinsella* genus, *Bifidobacterium* genus, *Bifidobacterium longum, Bifidobacterium angulatum, Dialister invisus, Clostridium leptum*, Firmicutes, Actinobacteria, *Faecalibacterium, Ruminococcus, Eubacterium, Alistipes, Roseburia, Anaerofilum, Streptococcus, Turicibacter, Parabacteroides, Dorea, Veillonella, Akkermansia, Sporobacter, Ethanoligenens, Papillibacter, Holdemania, Weissella, Dialister, Pseudoramibacter, Streptococcus, Anaerovorax, Lactococcus, Leuconostoc, Ethanoligenens, Helcococcus, Alkaliphilus, Clostridium aldenense, Clostridium methylpentosum, Eubacterium ruminantium, Phascolarctobacterium faecium, Alistipes onderdonkii*, and *Bacteroides caccae*.

8. The method of claim 6, wherein a probiotic and/or a probiotic group is selected from the group consisting of *Bacteroides thetaiotaomicron, Bacteroides vulgatus, Bacteroides distasonis, Bacteroides fragilis, Bifidobacterium adolescentis* group, *Eubacterium aerofaciens, Clostridium ramosum, Escherichia coli, Streptococcus faecalis* group, *Lactobacillus* spp., *L. acidophilus*, gram-negative anaerobes, enterococci, *Bacteroides* sp., *Parabacteroides*, ara-

*bacteroides, Prevotella, Porphyromonas,* gram-positive anaerobic cocci, *Clostridium* sp., Enterobacteriaceae, *E. coli, L. bulgaricus, S. thermophilus, Collinsella genus, Bifidobacterium genus, Bifidobacterium longum, Bifidobacterium angulatum, Dialister invisus, Clostridium leptum,* Firmicutes, Actinobacteria, *Faecalibacterium, Ruminococcus, Eubacterium, Alistipes, Roseburia, Anaerofilum, Streptococcus, Turicibacter, Parabacteroides, Dorea, Veillonella, Akkermansia, Sporobacter, Ethanoligenens, Papillibacter, Holdemania, Weissella, Dialister, Pseudoramibacter, Streptococcus, Anaerovorax, Lactococcus, Leuconostoc, Ethanoligenens, Helcococcus, Alkaliphilus, Clostridium aldenense, Clostridium methylpentosum, Eubacterium ruminantium, Phascolarctobacterium faecium, Alistipes onderdonkii,* and *Bacteroides* caccae.

9. The method of claim 5, wherein a probiotic and/or a probiotic group is a probiotic mixture composed of at least one, preferably at least three, bacterial species in about the proportions found normally in the colon, wherein human colonic flora may comprise 1,000 or more bacterial species comprising gram-negative anaerobic rods, gram-positive non-spore-forming anaerobic rods, anaerobic cocci, *Clostridium, Streptococcus,* gram-negative aerobic or facultative rods, and aerobic or facultative organisms.

10. The method of claim 1, wherein *Desulfovibrio* overgrowth in the gastrointestinal tract of a patient is an increase in fraction of *Desulfovibrio* in total bacterial flora of stool from autistic patient over control.

11. The method of claim 10, wherein *Desulfovibrio* is selected from the group consisting of *Desulfovibrio desulfuricans, Desulfovibrio fairfieldensis, Desulfovibrio piger, Desulfovibrio intestinalis,* and *Desulfovibrio vulgaris* and a combination thereof.

* * * * *